(12) United States Patent
Gibby et al.

(10) Patent No.: US 11,989,341 B2
(45) Date of Patent: *May 21, 2024

(54) ALIGNMENT OF MEDICAL IMAGES IN AUGMENTED REALITY DISPLAYS

(71) Applicant: Novarad Corporation, American Fork, UT (US)

(72) Inventors: Wendell Arlen Gibby, Mapleton, UT (US); Steven Todd Cvetko, Draper, UT (US)

(73) Assignee: Novarad Corporation, Provo, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/589,679

(22) Filed: Jan. 31, 2022

(65) Prior Publication Data
US 2022/0155854 A1 May 19, 2022

Related U.S. Application Data

(63) Continuation of application No. 16/745,160, filed on Jan. 16, 2020, now Pat. No. 11,237,627.

(51) Int. Cl.
*G06F 3/01* (2006.01)
*G02B 27/01* (2006.01)
(Continued)

(52) U.S. Cl.
CPC ............ *G06F 3/012* (2013.01); *G02B 27/017* (2013.01); *G06T 7/0012* (2013.01); *G06T 19/006* (2013.01); *G16H 30/20* (2018.01)

(58) Field of Classification Search
CPC ....... G06F 3/012; G06F 3/011; G02B 27/017; G06T 7/0012; G06T 19/006; G16H 30/20;
(Continued)

(56) References Cited

U.S. PATENT DOCUMENTS

| 6,147,678 A | 11/2000 | Kumar et al. |
| 9,119,655 B2 | 9/2015 | Bowling et al. |

(Continued)

FOREIGN PATENT DOCUMENTS

| JP | 2014-131552 | 7/2014 |
| JP | 2017-146758 | 8/2017 |

(Continued)

OTHER PUBLICATIONS

Peters, T.M.: Image-guidance for surgical procedures. Phys. Med. Biol. 51 (14), R505-R540 (2006), 37 pages.

(Continued)

*Primary Examiner* — Ryan R Yang
(74) *Attorney, Agent, or Firm* — Thorpe North & Western, LLP.

(57) ABSTRACT

An AR headset is described to co-localize an image data set with a body of a person. One method can include identifying optical codes with a contrast medium in a tubing on the body of the person using the AR headset. The image data set can be aligned with the body of the person using the fixed position of the image visible marker with the contrast medium in the tubing with respect to the optical code referenced to a representation of the image visible marker. In one configuration, an image data set can be scaled by comparing a measured size of the image visible marker (e.g., gadolinium tubing) in the captured image data set to the known size of the image visible marker. In addition, a center of an optical code may be identified to more accurately align the image data set with a body of a person.

24 Claims, 14 Drawing Sheets

(51) Int. Cl.
*G06T 7/00* (2017.01)
*G06T 19/00* (2011.01)
*G16H 30/20* (2018.01)

(58) Field of Classification Search
CPC ........ G16H 40/63; A61B 90/39; A61B 90/96; A61B 2090/365; A61B 2090/372; A61B 2090/3925; A61B 2090/3937; A61B 2090/3954; A61B 2090/3966; A61B 2090/3995; A61B 2090/502
See application file for complete search history.

(56) References Cited

U.S. PATENT DOCUMENTS

| | | |
|---|---|---|
| 9,128,909 B2 | 9/2015 | Brindley |
| 9,161,824 B2 | 10/2015 | Chishti et al. |
| 9,572,516 B1 | 2/2017 | Sheikh |
| 9,589,348 B1 | 3/2017 | Linde |
| 10,478,149 B2 | 11/2019 | Tamersoy |
| 11,145,123 B1 | 10/2021 | Chor |
| 11,172,996 B1 | 11/2021 | Qian et al. |
| 11,287,874 B2 | 3/2022 | Gibby et al. |
| 11,432,879 B2 | 9/2022 | Kapoor |
| 2005/0259882 A1 | 11/2005 | Dewaele |
| 2005/0262031 A1 | 11/2005 | Saidi et al. |
| 2006/0152434 A1 | 7/2006 | Sauer et al. |
| 2007/0060799 A1 | 3/2007 | Lyon |
| 2007/0066881 A1 | 3/2007 | Edwards |
| 2008/0208041 A1 | 8/2008 | Gilboa |
| 2009/0278915 A1 | 11/2009 | Kramer et al. |
| 2010/0049548 A1 | 2/2010 | Kubota |
| 2010/0099980 A1 | 4/2010 | Godara et al. |
| 2010/0215213 A1 | 8/2010 | Mielekamp et al. |
| 2011/0105895 A1 | 5/2011 | Kornblau et al. |
| 2011/0268248 A1 | 11/2011 | Simon et al. |
| 2012/0078236 A1 | 3/2012 | Schoepp |
| 2012/0244939 A1 | 9/2012 | Braun |
| 2013/0197354 A1 | 8/2013 | Maschke et al. |
| 2014/0062900 A1 | 3/2014 | Kaula et al. |
| 2014/0275760 A1 | 9/2014 | Lee et al. |
| 2014/0318699 A1 | 10/2014 | Longinotti-Buitoni |
| 2014/0355840 A1 | 12/2014 | Pearson Peyton |
| 2015/0161802 A1 | 6/2015 | Christiansen |
| 2015/0168729 A1 | 6/2015 | Kobayashi |
| 2015/0173715 A1 | 6/2015 | Raghavan et al. |
| 2016/0035139 A1 | 2/2016 | Fuchs et al. |
| 2016/0143699 A1 | 5/2016 | Tanji |
| 2016/0166333 A1 | 6/2016 | Wang et al. |
| 2016/0180441 A1 | 6/2016 | Hasan et al. |
| 2016/0188941 A1 | 6/2016 | Todeschini |
| 2016/0220393 A1 | 8/2016 | Slivka et al. |
| 2016/0259428 A1 | 9/2016 | Hou et al. |
| 2016/0270853 A1 | 9/2016 | Lavallee et al. |
| 2017/0045938 A1 | 2/2017 | Aoyama et al. |
| 2017/0065832 A1 | 3/2017 | Berlinger |
| 2017/0071686 A1 | 3/2017 | Birkenbach et al. |
| 2017/0116729 A1 | 4/2017 | Stolka et al. |
| 2017/0165008 A1 | 6/2017 | Finley |
| 2017/0178540 A1 | 6/2017 | Rios et al. |
| 2017/0196513 A1 | 7/2017 | Longinotti-Buitoni |
| 2017/0249745 A1 | 8/2017 | Fiala |
| 2017/0273654 A1 | 9/2017 | Taguchi et al. |
| 2017/0296292 A1 | 10/2017 | Mahmood et al. |
| 2017/0368369 A1 | 12/2017 | Heinrich |
| 2018/0064410 A1 | 3/2018 | Li et al. |
| 2018/0092698 A1 | 4/2018 | Chopra et al. |
| 2018/0177403 A1 | 6/2018 | Kim-Whitty |
| 2018/0247128 A1 | 8/2018 | Alvi et al. |
| 2018/0303558 A1 | 10/2018 | Thomas |
| 2018/0321894 A1 | 11/2018 | Paulovich |
| 2018/0322702 A1 | 11/2018 | Djajadiningrat |
| 2018/0373327 A1 | 12/2018 | Todeschini |
| 2019/0075456 A1 | 3/2019 | Evans |
| 2019/0108645 A1 | 4/2019 | Ben-Yishai |
| 2019/0209080 A1 | 7/2019 | Gullotti et al. |
| 2019/0236816 A1 | 8/2019 | Wang |
| 2019/0287306 A1 | 9/2019 | Wieser |
| 2019/0310819 A1 | 10/2019 | Xu et al. |
| 2019/0317719 A1 | 10/2019 | Baer |
| 2019/0328462 A1 | 10/2019 | Liu et al. |
| 2019/0348169 A1 | 11/2019 | Gibby et al. |
| 2019/0380792 A1 | 12/2019 | Poltaretskyi et al. |
| 2020/0058169 A1 | 2/2020 | Friesenhahn |
| 2020/0138518 A1 | 5/2020 | Lang |
| 2020/0145495 A1 | 5/2020 | Coffey |
| 2020/0159313 A1 | 5/2020 | Gibby et al. |
| 2020/0186786 A1 | 6/2020 | Gibby et al. |
| 2020/0188030 A1 | 6/2020 | Kopper |
| 2020/0197107 A1 | 6/2020 | Ryan et al. |
| 2020/0225814 A1 | 7/2020 | Norieda |
| 2020/0242755 A1 | 7/2020 | Schneider |
| 2020/0286222 A1 | 9/2020 | Essen |
| 2020/0405395 A1 | 12/2020 | Gullotti et al. |
| 2021/0045838 A1 | 2/2021 | Bradbury et al. |
| 2021/0049921 A1 | 2/2021 | Welch et al. |
| 2021/0137634 A1 | 5/2021 | Lang |
| 2021/0186355 A1 | 6/2021 | Ben-Yishai et al. |
| 2022/0130116 A1 | 4/2022 | McCall |
| 2022/0151705 A1 | 5/2022 | Nikou et al. |
| 2022/0202493 A1 | 6/2022 | Gibby et al. |
| 2022/0287676 A1 | 9/2022 | Steines et al. |
| 2022/0291741 A1 | 9/2022 | Gibby et al. |
| 2023/0072188 A1 | 3/2023 | Gibby et al. |
| 2023/0169740 A1 | 6/2023 | Gibby et al. |

FOREIGN PATENT DOCUMENTS

| | | |
|---|---|---|
| WO | WO 2014/200016 | 12/2014 |
| WO | WO 2018-063528 | 4/2018 |
| WO | WO 2018/132804 | 7/2018 |
| WO | WO 2018/134140 | 7/2018 |
| WO | WO 2019/238209 | 12/2019 |
| WO | WO 2020123702 | 6/2020 |

OTHER PUBLICATIONS

Fabrizio Cutolo, Augmented Reality in Image-Guided Surgery, Nov. 2017, 12 pages.

ALIGNMENT OF MEDICAL IMAGES IN AUGMENTED REALITY DISPLAYS

PRIORITY DATA

This application is a continuation of U.S. patent application Ser. No. 16/745,160, entitled "Alignment of Medical Images in Augmented Reality Displays" filed Jan. 16, 2020, which is incorporated herein by reference.

BACKGROUND

Mixed or augmented reality is an area of computing technology where images from the physical world and virtual computing worlds may be combined into a mixed reality world. In mixed reality, people, places, and objects from the physical world and virtual worlds become a blended environment. A mixed reality experience may be provided through existing commercial or custom software along with the use of VR (virtual reality) or AR (augmented reality) headsets.

Augmented reality (AR) is an example of mixed reality where a live direct view or an indirect view of a physical, real-world environment is augmented or supplemented by computer-generated sensory input such as images, sound, video, graphics or other data. Such augmentation may be performed as a real-world location is viewed and in context with environmental elements. With the help of advanced AR technology (e.g. adding computer vision and object recognition) the information about the surrounding real world of the user becomes interactive and may be digitally modified (e.g. via computer graphic overlays).

An issue faced by AR systems or AR headsets is identifying a position and orientation of an object with a high degree of precision. Similarly, aligning the position of a virtual element with a live view of a real-world environment may be challenging. For example, aligning a virtual object with a physical object as viewed through an AR headset may be difficult because the luminescence or light of the virtual object tends to obscure the underlying physical object with which the virtual object is to be aligned. Providing an approximate alignment of a virtual object with a physical object to within a few centimeters may be useful for entertainment and less demanding applications but greater positioning and alignment resolution for AR systems may be desired in the scientific, engineering and medical disciplines. As a result, positioning and alignment processes for AR used in the scientific, engineering and medical disciplines may be done manually which can be time consuming, cumbersome, and inaccurate.

DETAILED DESCRIPTION

A technology is provided for using an augmented reality (AR) headset to identify one or more optical codes (e.g., an AprilTag, QR code, or 2D optical bar code) that are in view of a camera of the AR headset during a medical procedure. The image data set can be aligned with a body of a person using one or more optical codes and image visible markers on the body of the person. The image data set may be a previously acquired image of a portion of body of a person using a non-optical imaging modality. Examples of the non-optical imaging modalities may be an MRI (magnetic resonance imaging) modality, CT (computed tomography) scanning modality, X-ray modality, Positron Emission Tomography (PET) modality, an ultrasound modality, a fluorescence modality, an Infrared Thermography (IRT) modality, 3D Mammography, or a Single-Photon Emission Computed Tomography (SPECT) scan modality, etc. The image data set can be aligned to the body of the person using an image visible marker that is a fixed distance from (e.g., to the side of or underneath) at least one optical code located on the body of the person. For example, an image visible marker and an optical code may both be attached onto one piece of material (e.g., co-located or in fixed proximity of each other) to facilitate the alignment of the image data set with the body of the person. An image visible marker is a marker that can be viewed in a non-visible imaging modality, such as a captured radiology image or an image data set, which may not be optically visible to the AR headset. The image data set may be captured with a representation of the image visible marker in machine captured images that capture structures of the human body with a non-optical imaging modality. The representation of the image visible marker in the image data set may be aligned with the body of the patient using the known fixed position of the image visible marker with respect to the one or more optical codes affixed on the body of the person (as described in further detail later). For example, the image visible marker may be an enclosed container (e.g., an MRI bead or sphere) or a contrast medium for MRI in a tubing that has a length. In other imaging modalities as mentioned above, an appropriate contrast medium can be provided in a tubing that is visible in an image captured in the respective modality (nuclear based image acquisition, etc.).

Figure 1:
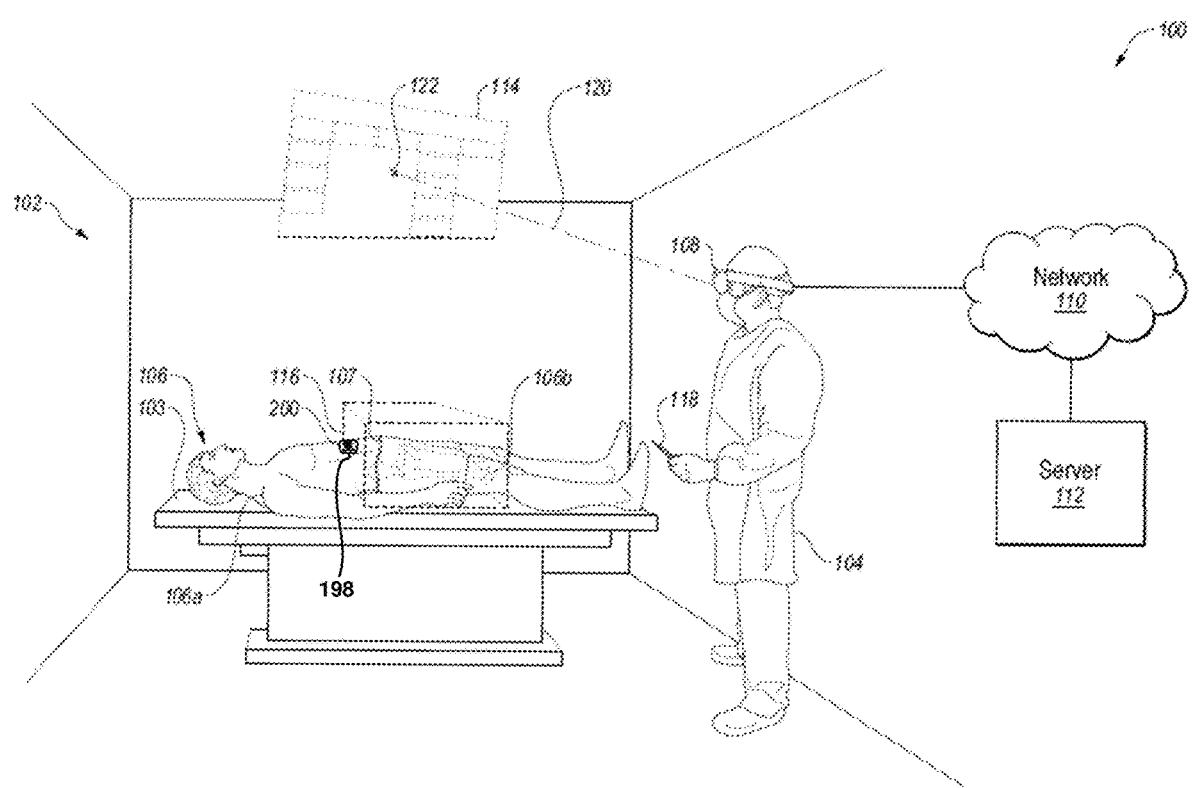
FIG. 1 illustrates an example augmented reality (AR) environment in which an image data set of a patient may be referenced and aligned to actual views of the patient using one or more visible optical codes fixed to a contrast medium or contrast marker in tubing attached to the visible optical codes.

FIG. 1 illustrates an example of an augmented reality (AR) environment 100 in which an image data set 116 of a patient or person 106 may be aligned with actual views of the patient 106 using an optical code 200 affixed to the patient 106. The image data set 116 may include imaging of tubing 198 or an enclosed container containing an image visible fluid, image visible medium, or image visible marker in the image data set. The identity of the separate optical tags 200 (e.g., unique optical codes) in the image data set 116 may be determined or encoded based on the location of the tubing 198 containing the image visible medium or marker and the length of the tubing. The optical code 200 may also be identified in camera images captured by the AR headset 108 using a visible AprilTag or 2D barcode as the optical code. Thus, the image visible marker 198 may be identified in the image data set 116 and may be aligned with the optical code 200 that is visible through the AR headset 108.

The environment 100 may include a physical space 102 (e.g., operating theater, a lab, etc.), a user 104, the patient 106, multiple optical codes 200 on the patient, a medical implement 118 with an optical code 198, and an AR headset 108 in communication with a server 112 over a computer network 110. A virtual user interface 114 and a virtual cursor 122 are shown in dashed lines to indicate that these virtual elements are generated by the AR headset 108 and are viewable by the user 104 through the AR headset 108.

The AR headset 108 may be an AR computing system that is capable of augmenting actual views of the patient 106 (covered by a hospital gown or fabric 107) with an image data set 116. For example, the AR headset 108 may be employed by the user 104 in order to augment actual views of the patient 106 with one or more 3D image data set views or radiologic images of the patient 106 including, but not limited to, bones (as illustrated in FIG. 1), muscles, organs, or fluids 106b.

The AR headset 108 may allow an image data set 116 (or a projection of the image data set) to be dynamically reconstructed. So, as the user 104 moves around the patient 106, the sensors of the AR headset 108 determine the location of the user 104 relative to the patient 106, and the internal anatomy of the patient displayed using the image data set can be reconstructed dynamically as the user 104 chooses different orientations relative to the patient. For example, the user 104 may walk around the patient 106. Then the AR headset 108 may augment actual views of the patient 106 with one or more acquired radiology images or image data sets (MRI, CT scan, etc.) of the patient 106, so that both the patient 106a and the image data set 116 of the patient 106a may be viewed by the user 104 from any angle (e.g., a projected image or a slice from the image data set may also be displayed). The AR headset 108 may be a modified version of the Microsoft HOLOLENS, Meta Company META 2, Epson MOVERIO, Garmin VARIA VISION or other AR headsets.

The optical code(s) 200 may be affixed to the patient 106 prior to the generation of image data of the patient 106 (e.g., capture of the MRI, CT scan, X-ray, etc.), and then remain affixed to the patient 106 while the patient 106 is being viewed by user 104 through the AR headset 108. Then, the optical code 200 and the image visible marker 198 may be employed by the AR headset 108 to programmatically align the image data set 116 of the patient 106 with actual views of the patient 106. For example, one or more optical codes 200 associated with the body of the person 106 can be identified. The optical code 198 on a body of the person 106a can be located in a fixed position relative to an image visible marker 198 that includes a contrast medium in tubing or a length of tubing. The image visible marker 198 that uses the contrast medium in a length of tubing can be identified in the image data set 116 acquired using a medical imaging device. The image data set 116 may be aligned with the body of the person 106b as viewed through the AR headset 108 using one or more optical codes 200 on the body of the person and using the fixed position of the image visible marker 198 with the contrast medium in the tubing with respect to the optical code 200. The representation of the image visible marker 198 with the contrast medium in the tubing in the image data set can be used as a reference point for the alignment process.

The contrast medium or contrast agent may be an MRI (magnetic resonance imaging) visible contrast medium. In one example, the encapsulated contrast medium or contrast agent in an enclosed container or tubing may be a paramagnetic fluid or semi-fluid. The contrast medium may be encapsulated in the enclosed container or tubing of a defined length or a variable length selected by a person. The defined length of the tubing may be linked with or identify an optical code with a 2D data encoding that is visible using the optical sensor of the AR headset. The defined length of the tubing may be associated with an optical code viewable by the camera or optical sensor of the AR headset by linking the defined length of tubing with the optical code in a data store or database. This registration or linkage between the visible optical code and the tubing may be done by capturing an image of the optical code with the tubing at a fixed distance from the optical code and recording the measured length of the captured tubing or by hand entry.

The segments of the tubing may vary (e.g., 3 mm, 5 mm, 7 mm, 10 mm) and a specific length of tubing may be associated with a separate optical code. For example, optical code A may have tubing attached to the optical code that is 5 millimeters (mm) long, optical code B may have tubing attached that is 7 mm long, and optical code C may have a tubing that is 10 mm long. The segments of the tubing may be linked to the respective optical code. Thus, when the image visible marker 198 created by the tubing with a specific length or enclosed container is identified in the image data set 116 then the corresponding optical code and the optical code's location is also known relative to the image data set.

The corresponding optical code 200 is known to be a fixed distance and orientation from the image visible marker with the tubing or enclosed container. The length of the sections of tubing can be used to align the image data with the visible body of the patient because each of the segments of the individual tubing may be different. Matching the image visible markers made of tubing with the representation of the tubing in the image data set and/or the optical code can be performed using the length of the tubing because each length or combination of multiple segments of tubing may be unique. As a result, the length of tubing cannot be matched to the incorrect optical code because the data store of links between the segments of tubing and the optical codes will be checked and a mismatch will be prevented. In addition, if a 5 mm tubing representation in the image data set is tried to be matched to visible or expected 10 mm tubing for an optical code, this results in a mismatch and the system will try to match the correct tubing length with the correct tubing representation.

In one example, a different size, shape or length of tubing 198 can be placed in a fixed position by the optical code 200. Each optical code (e.g., AprilTag or 2D bar code) has a unique optical code 200 but the optical codes are not visible in the image data set. The tubing that is visible in the image data set identifies: 1) where the visible optical code is and 2) which visible optical code is associated with the image visible code. Once the position of the tubing is known then the position of the visible optical code 200 is also known. Finding the position of the optical code 200 and the tubing allows the system to join the image data set (e.g., an MR image) with the real view or visible view of a person's body through the A/R headset.

The tubing that contains the contrast medium or contrast agent may be a shaped tubing in the shape of: a line, a cross formation, concentric circles, a square, a rectangle, a right angle, or a grid formation. The shapes described may be created in a single plane with other tubing segments in the shape (however the tubing does have three-dimensional depth due to the tubing diameter). The tubing can have a cross-sectional shape that is at least one of: round, triangular, square, rectangular, elliptical, hexagonal, octagonal, oval, semi-circle, or polygonal. The encapsulated contrast medium or contrast agent can be a gadolinium solution (e.g., a gadolinium chelate), copper sulfate, iron solution, manganese, vitamin E oil, or other magnetic resonance visible medium. The tubing may be a plastic tubing, glass tubing, composite tubing (e.g., glass and epoxy), or another non-metal tubing. The shape of the image visible marker can be used to determine which unique optical code or visual marker is at the location of the unique image visible marker.

Further, the same optical code 200 used during the capturing of the image data set 116 may be used to automatically retrieve the image data set to ensure that the image data set retrieved by the AR headset 108 matches the actual patient 106 being viewed through the AR headset 108. Similarly, the tubing 198 length or shape may also be to validate that correct patient is having the procedure performed and this can be checked against the image data set (e.g., checking the tubing patterns are correct for the patient). If a patient has tubing patterns that do not match the image data set (or vice versa) then an error can be flagged.

The virtual user interface 114 generated by the AR headset 108 may include options for altering the display of the projected inner anatomy of the patient 106 from the image data set 116 of the patient 106. The virtual user interface 114 may include other information that may be useful to the user 104. For example, the virtual user interface 114 may include information about the patient or the medical implements 118 (e.g., medical instruments, implants, etc.) being identified with an optical code. In another example, the virtual user interface 114 may include medical charts or other medical data of the patient 106. In some configurations, the image data 116 or captured radiological data of a person may be displayed by the AR headset 108 using a volume of the image data set 116 to display radiologically captured anatomy (e.g., bones 106b, tissue, vessels, fluids, etc.) of the patient 106a from the image data. This image data may contain axial slices, coronal slices, sagittal slices, or oblique slices of the image data. Slices may be two-dimensional (2D) slices, three-dimensional (3D) slices, and/or four dimensional (4D) slices (3D images with a time sequence of images) that have a depth as well as a height and width (e.g., one or more layers of voxels). A user 104 may control the virtual user interface 114 using: hand gestures, voice commands, eye movements, remote controls (e.g., a finger clicker), a 3D mouse, a VR wand, finger sensors, haptic technology, or other control methods.

Figure 2:
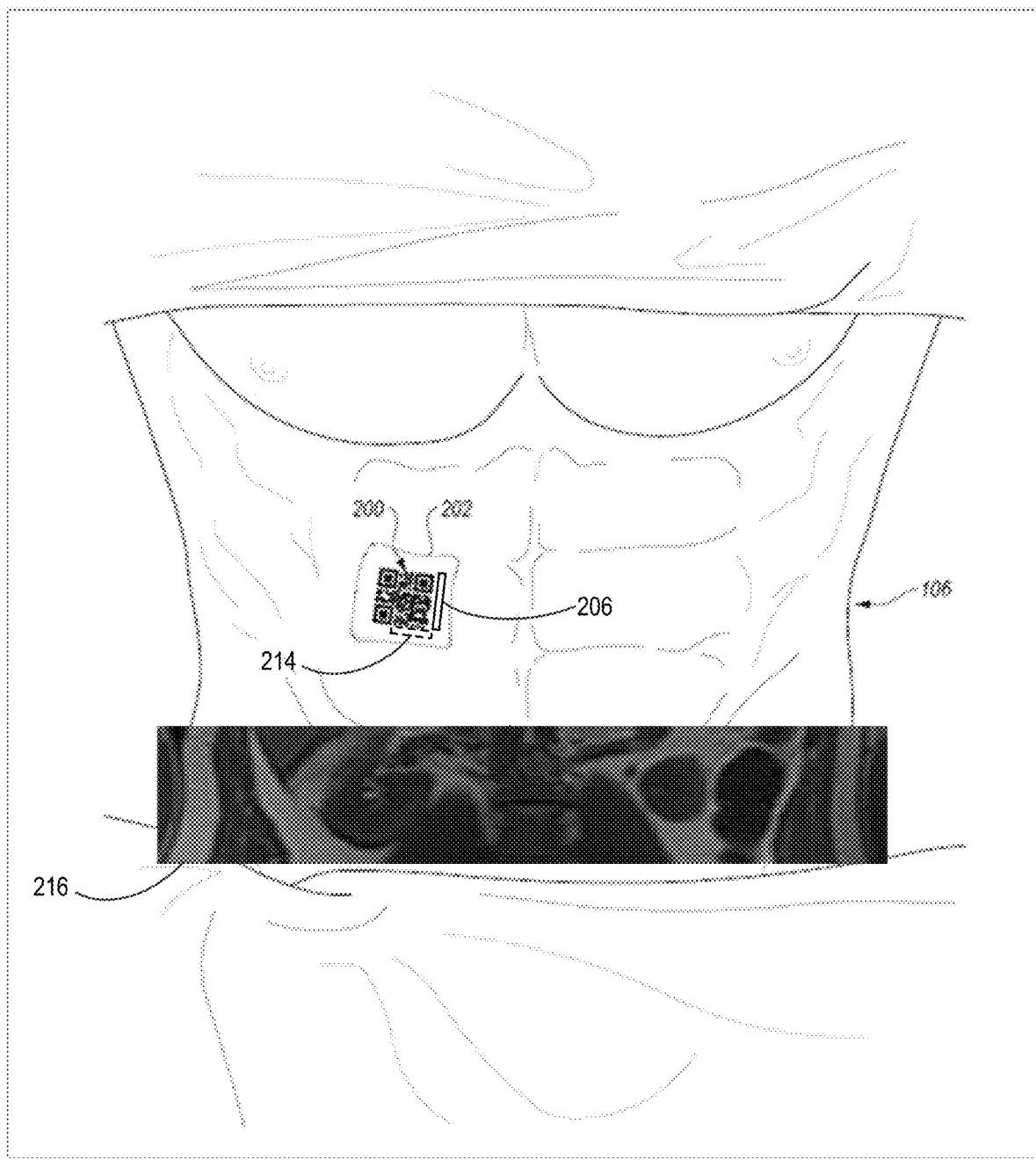
FIG. 2 illustrates an example of an optical code with an image visible marker which is tubing affixed to the optical code and patient.

FIG. 2 illustrates the optical code 200 of FIG. 1 affixed to the patient 106 of FIG. 1. With reference to both FIG. 1 and FIG. 2, the optical code 200 may be perceptible to an optical sensor, such as an optical sensor or camera for the visual spectrum built into the AR headset 108. In some embodiments, the optical code 200 may be an AprilTag, a linear barcode, a matrix two-dimensional (2D) barcode, a Quick Response (QR) code, or some combination thereof. An AprilTag is a two-dimensional bar code which may be a visual fiducial system which is useful for augmented reality and camera calibration. The AprilTags may be used to compute the 3D position, orientation, and identity of the tags relative to a camera, sensor, or AR headset.

The optical code 200 may further be associated with markers 206, 214 or image visible markers that are perceptible to a non-optical imaging modality. One example of a non-optical imaging modality used to capture the image visible marker with a tubing containing paramagnetic fluid may be an MRI modality. In another example, the non-optical images or image data sets may be an image or image data set which includes a combination of two or more forms of non-optical imaging modality (e.g., two or more images combined together, combined segments of two or more non-optical images, a CT image fused with an MRI image, etc.). Each image data set in a separate modality may have an image visible code in the individual image data set which may allow a PET image, a CT image, an MRI image, a fluoroscopy image, etc., to be aligned and referenced together with an optical code on a body of a person in an AR system view. Forming the markers 206 from a material that is perceptible to a non-optical imaging modality may enable the markers 206 or image visible markers to appear in an image data set of the patient 106 that is captured using any combination of non-optical imaging modalities.

The markers 206 or image visible markers may have one or more segments of tubing containing paramagnetic fluid 206. The segments of tubing may be provided individually as in FIG. 2 or may be arranged in a pattern and may have a fixed position relative to a position of the optical code 200. Multiple markers 214 or multiple sections of tubing with paramagnetic material may optionally be used to form a recognizable pattern that identifies a location and/or the image visible markers. For example, in the embodiment disclosed in FIG. 2, the optical code 200 may be printed on a material 202 (such as an adhesive bandage, paper, plastic, etc.) and the markers 206 may be affixed to the material 202 (e.g., attached or glued to the material 202). In this embodiment, one or more markers 206 may be arranged in a fixed position relative to a position of the optical code 200 by being arranged in the fixed position with respect to the bandage 202 or material.

Additionally, the markers 206 may be arranged by affixing or printing (at least temporarily) the optical code 200 directly on the skin 106a of the patient 106. By arranging the markers 206 in a pattern on the skin of the patient 106 that has a fixed position relative to a position of the optical code 200, this fixed position may be employed to calculate the location of the pattern of the markers 206 or image visible markers with respect to a visible location of the optical code 200. Then the visibility of markers 206 or tubing to sensors of the AR headset 108 may also be used for alignment.

Once the optical code 200 and the markers 206 are affixed to the patient 106 in a fixed pattern, the non-optical imaging modality (to which the markers 206 are perceptible) may be employed to capture an image data set 216 (only a partial segment shown) of the patient 106 and of the markers 206. In particular, the image data may include internal anatomy (such as bones 106b, muscles, organs, or fluids) of the patient 106, as well as including the pattern of markers 206, 214 in a fixed position relative to the positions of the inner anatomy of the patient 106. In other words, not only will the internal anatomy of the patient 106 appear in the image data of the patient 106, but the markers 206 will also appear in the image data set of the patient 106 in a pattern, and the position of this pattern of the markers 206 will appear in the image data set in a fixed position relative to the positions of the internal anatomy of the patient 106. In one example, where the non-optical imaging modality is an MRI modality, the MRI images may display the bones, organs, and soft tissues of the patient 106, as well as the markers 206 with tubing arranged in a fixed position with respect to the positions of the bones, organs, and soft tissues of the patient 106.

Further, the patient 106 may be moved, for example, from a medical imaging room in a hospital to an operating room in the hospital. Then a user 104 (such as a medical professional in FIG. 1) may employ the AR headset 108 to determine a location of the optical code 200 (and optionally the visible portion of the markers 206 if viewable) on the body of a person or patient. Next, the AR headset 108 may automatically retrieve the image data of the patient 106 based on the optical code.

After detecting the optical code 200 in the 3D space 102, the AR headset 108 may automatically calculate the position of one or more markers 206 with tubing in the 3D space 102 with respect to one another. This automatic calculation may be based on: the sensed position of the optical code 200 in the 3D space 102, the known fixed position of the pattern of the markers 206 with tubing relative to the position of the optical code 200 or visually viewing the segments of tubing filled with paramagnetic fluid. Even where the markers 206 are not perceptible to the AR headset 108 (for example, due to the markers 206 being transparent plastic or underneath an optical code printing material), the AR headset 108 can automatically calculate the location of the pattern of the marker(s) 206 based on the position of the optical code 200 and on the fixed position of the pattern of the marker(s) 206 relative to the position of the optical code 200. In this example, these fixed positions may enable the AR headset 108 to automatically calculate the position of the pattern of the marker(s) 206 in the 3D space 102 with respect to one another even where the AR headset 108 is not directly sensing the positions of the markers 206.

After calculating the location of the pattern of the markers 206 or image visible markers in the 3D space 102, the AR headset 108 may then register the position of the internal anatomy of the patient 106 in the 3D space 102 by aligning the calculated position of the pattern of the marker(s) 206 in the 3D space 102 with the position of the pattern of the marker(s) 206 in the image data set. The alignment may be performed based on the calculated position of the pattern of the markers 206 with tubing in the 3D space 102 and the fixed position of the image data set to the markers 206. This alignment and registration may then enable the AR headset 108 to display, in real-time, the internal anatomy of the patient 106 from the image data projected onto actual views of the patient 106. Thus, the optical code 200, and the one or more associated markers 206, may be employed by the AR headset 108 to automatically align the image data of the patient 106 with actual views of the patient 106.

Figure 3:
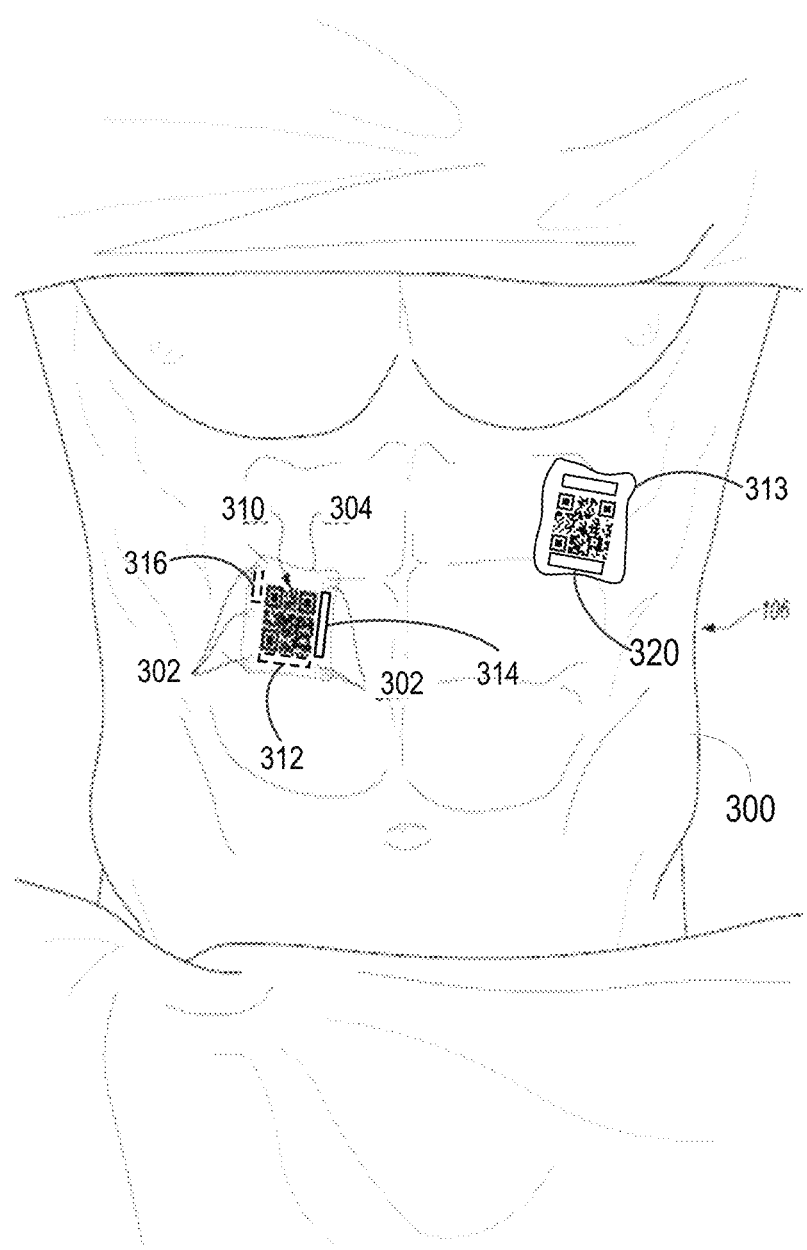
FIG. 3 illustrates an example of the use of multiple segments of tubing as image visible markers.

FIG. 3 illustrates that multiple optical codes 312, 313 may be simultaneously affixed to the patient 106 in order to further ensure accurate alignment of an image data set of the patient 106 with actual views of the patient 106 in the 3D space 102. Also, the pattern of markers 314, 312 for each optical code 310 may use multiple segments of tubing. Further, since the markers 314 are affixed to an outside layer of the patient 106, the markers 314, 312 may not all be in one actual plane, but instead may conform to any curvatures of the outside layer of the patient 106. In these embodiments, the position of the pattern of the markers 314, 312 relative to a position of the optical code 304 may be established after affixing the optical code 310 and the markers 314, 312 to the patient 106 to account for any curvatures on the outside layer of the patient 106.

FIG. 3 further illustrates a visual image that may be captured by the camera of the AR headset or AR system. The visual image may include a body 300 of a patient with an optical code 310 printed on a material 304 that is affixed to the body 300 of the patient 106. A first marker 314 is shown that is oriented substantially perpendicular to a second marker 312. The first marker 314 and second marker 312 may be tubing that contains paramagnetic fluid. The use of a second marker 312 or a third marker 316 may be optional and is illustrated using dashed lines. Using multiple orientations for the markers may be useful because the multiple markers can assist with orienting the image data set in the right orientation and avoid a flipped or inverted image. FIG. 3 further illustrates that an image visible marker 320 with a tube on a second optical code 313. The image visible markers may run at any orientation with respect to the optical code. The orientation of the marker 320 may run parallel to an edge of the optical code, perpendicular to an edge of the optical code, or askew to the edges of the optical code. In addition, optional radiopaque markers 302 may be included with the optical code for use in image alignment with imaging modalities other than MRI, as discussed earlier.

In another configuration, the tubing may include a plurality of tubing sections each having a separate length which are at a fixed distance and orientation to the optical code 200. For example, each optical code 200 may have two or three sections of tubing attached to the optical code 200. For example, three different segments of tubing may be oriented the same way and the combination of segments of tubing is unique and also identifies the unique optical code. Alternatively, each section of tubing may extend from a separate corner or vertex of the optical code 302.

The use of tubing with paramagnetic fluid as an image visible marker can assist with alignment in the MRI (Magnetic Resonance Imaging) environment because the use of iron or metallic materials in MRI images tends to cause artifacts in the MRI image. More specifically, the use of iron or metallic material in MR imaging produces attenuation, loss, or destruction of the signal created by the protons of water molecules where iron or metallic materials are used in MRI imaging. Accordingly, the present technology can use a marker in an MRI image that is a polyethylene tubing filled with paramagnetic material such as gadolinium fluid.

Figure 4A:
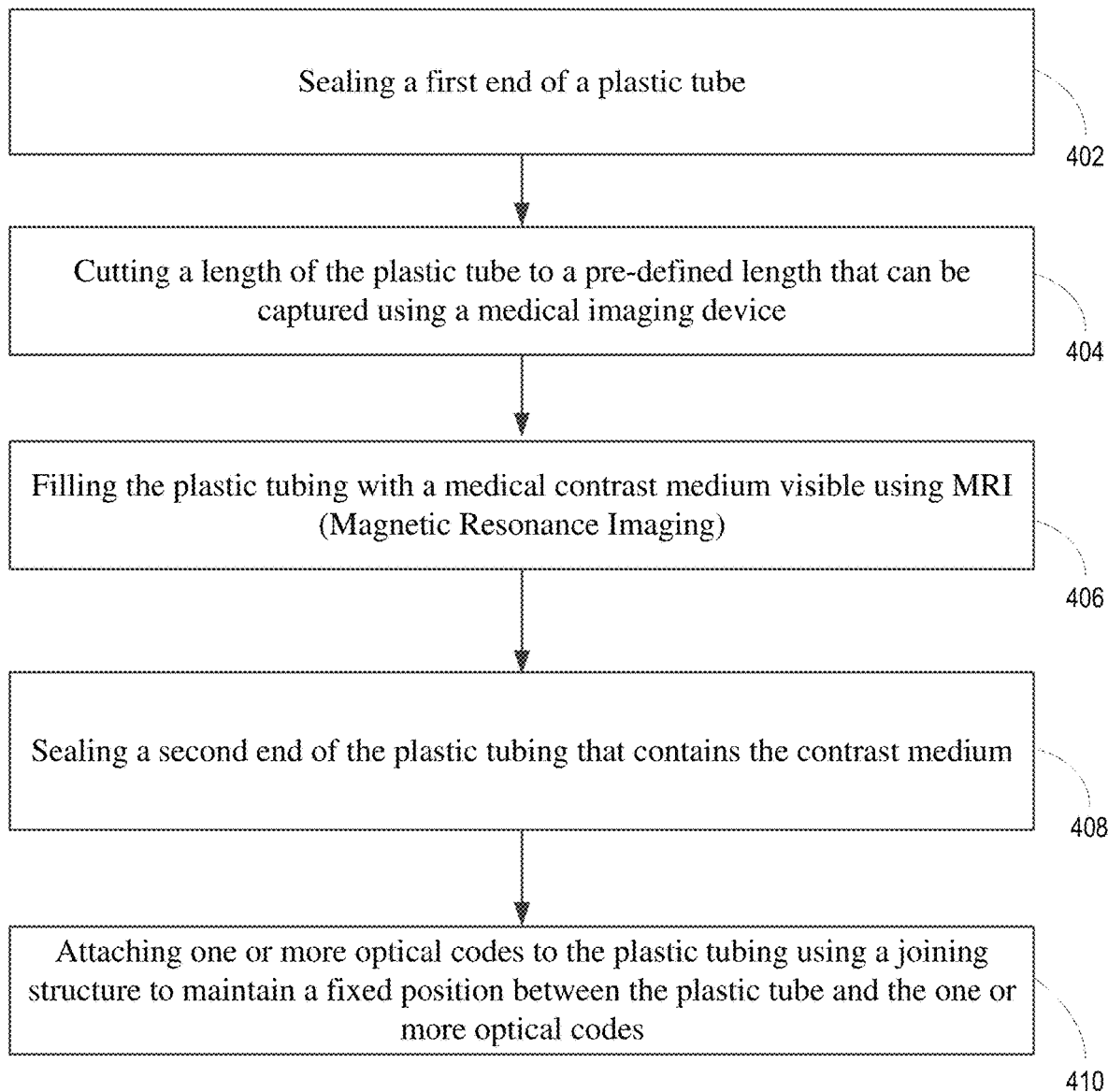
FIG. 4a is a flow chart illustrating a method for manufacturing an encapsulated contrast medium or contrast marker in a tubing that is fixed to an optical code.

FIG. 4a is a flowchart illustrating a method for manufacturing an encapsulated contrast medium or contrast marker in tubing. One operation can be sealing a first end of plastic tubing, as in block 402. The plastic tubing can be sealed using a heated wire to cut and seal the first end of the tubing. Alternatively, a heated knife, heated crimping tool or another heated sealing tool may also be used to seal the first end of the plastic tubing.

Another operation is cutting a length of the plastic tubing to a defined or measured length that can be captured using a medical imaging device, as in block 404. The plastic tubing length can be cut to any length that can be captured by a medical imaging device. For example, the length of the plastic tubing may be just a few millimeters in size up to many centimeters, as may be useful for the imaging scenario. The size of the plastic tubing is preferably less than size of the imaging window which the medical imaging device (e.g., MRI device) is expected to capture.

The plastic tubing may be filled with a contrast medium or contrast marker visible in an MRI image, as in block 406. The contrast medium may be paramagnetic fluid, such as a gadolinium fluid or another contrast agent which is visible to an MRI imaging device, as described earlier. A second end of the plastic tubing that contains the image contrast medium may be sealed, as in block 408. The material in the tubing can include paramagnetic material and a fluid, and the paramagnetic fluid will show up as a bright area in a 3D MRI image. In other words, the contents of the tubing will be visible in the MRI image.

One or more optical codes may be attached to the plastic tubing using a joining or mounting structure to maintain a fixed position between the plastic tubing and the one or more optical codes, as in block 410. The joining or mounting structure may be the paper or plastic the optical code is printed on or the joining structures may be any paper, plastic structure or non-metal structure used to fix the distance and orientation between the optical code and the tubing. Thus, the tubing can be used to identify a location of the optical code or encode the position of the unique optical code by using the size (e.g., length or diameter), shape or other geometry of the tubing.

Figure 4B:
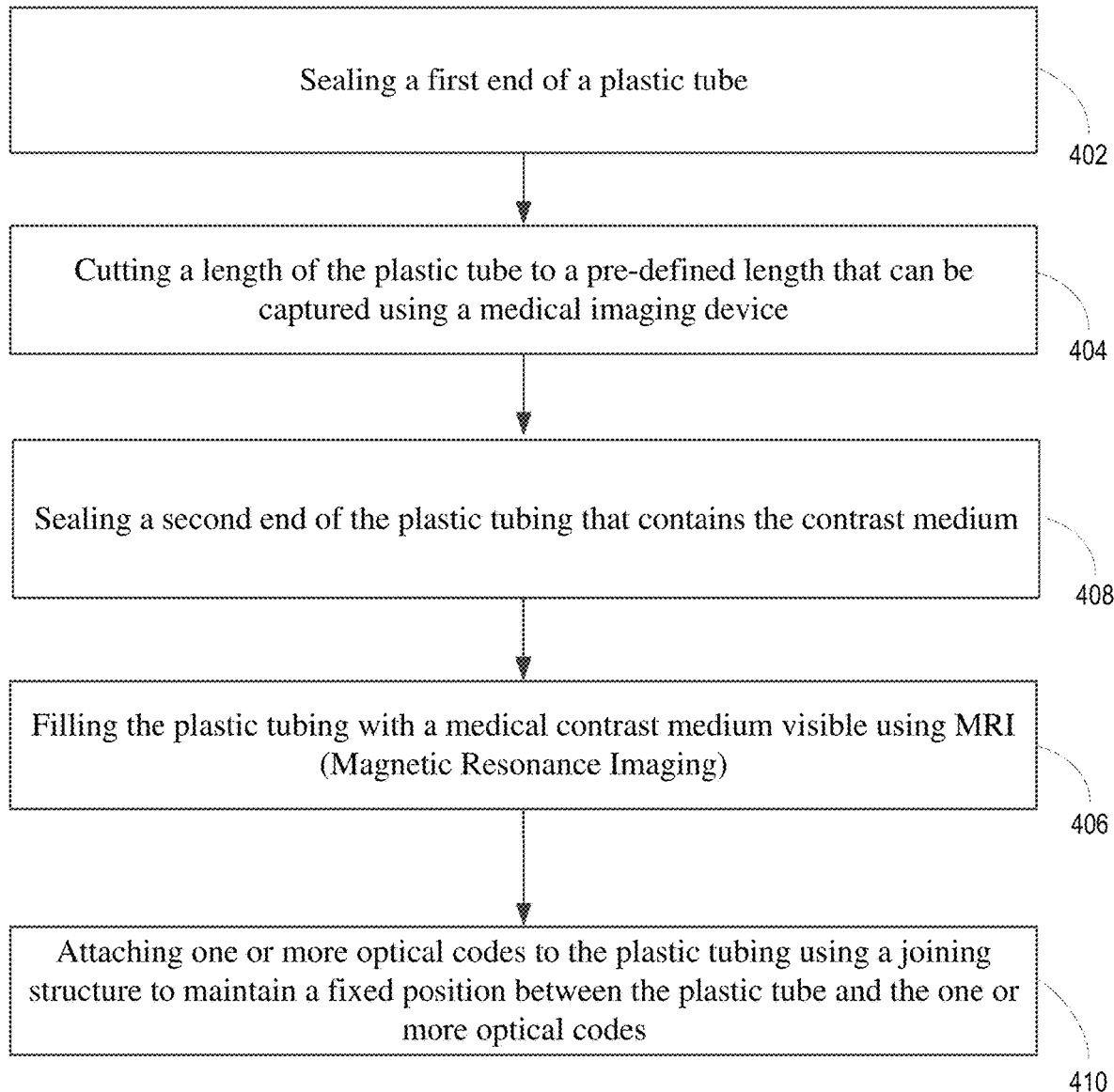
FIG. 4b is a flow chart illustrating an alternate ordering for a method for manufacturing an encapsulated contrast medium or contrast marker in a tubing that is fixed to an optical code.

FIG. 4b illustrates that the second end of the plastic tubing may be sealed before the fluid is added to the plastic tubing, 408. In this ordering of the method, the plastic tubing may be filled with a medical contrast medium visible using MRI after the plastic tubing is sealed, as in block 406. In this situation, the contrast medium may be injected into the plastic tubing and the injection hole may be sealed using heat or an adhesive material over the injection hole. For example, a dilute paramagnetic solution like gadolinium, copper sulfate or iron solution may be filled through one end of the tubing before the tubing is closed off.

The tubing described in FIGS. 4a and 4b may also be sealed off with other sealing agents. Examples of other sealing agents or methods may include plugging the end of the tubing with glue, using a clay sealant plug, applying an adhesive plastic layer over the end, affixing a plastic end cap at the end of the tubing, adhering metal foil over the end, adhering metalized plastic sheets to the tubing, or using any other sealing method or materials.

Figure 5:
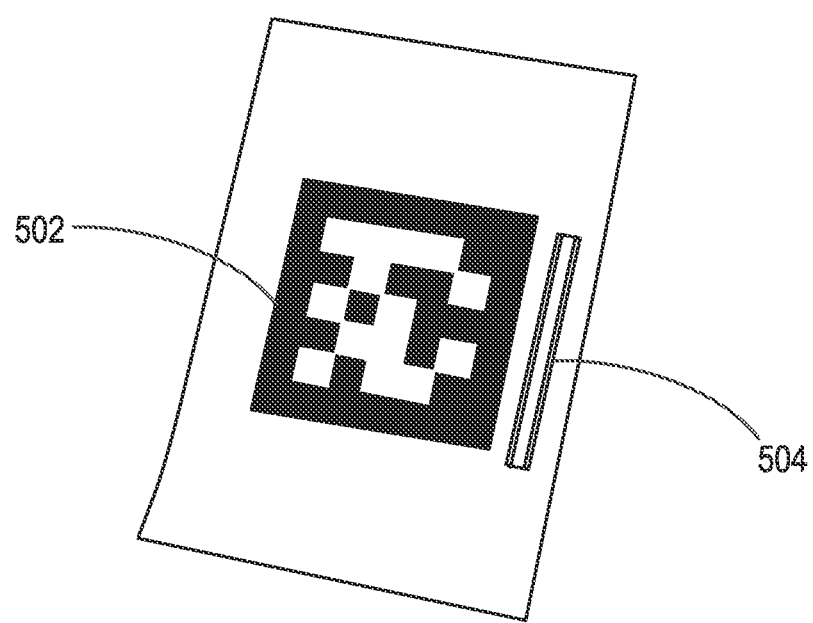
FIG. 5 illustrates example of a view of an AprilTag with attached tubing containing a contrast medium or a contrast marker.

FIG. 5 illustrates an optical code 502 and tubing 504 containing an image visible marker or image visible medium. The optical code may be an AprilTag (as illustrated), a 2D bar code or other optical codes that may be captured with a camera. The tubing 504 may have a length that is similar to the length of a side or edge of the optical code 502. However, the size of the length of tubing may be shorter or longer than the length of an edge of the optical code 520. In addition, the length of tubing is shown as being substantially parallel to the side of the optical code but the length of tubing may be set at any angle with respect to the optical code 520. For example, the tubing may be a ten-degree angle with respect to the optical code 520 or it may be perpendicular to the side of the optical code. The tubing may also be a plastic that is bendable which may allow the tubing to deform to follow the contour of body of the patient or the anatomy being imaged. Even when the tubing is curved, the medical imaging tools are able to measure the path of the tubing in 3D and determine the length of the tubing.

Figure 6A:
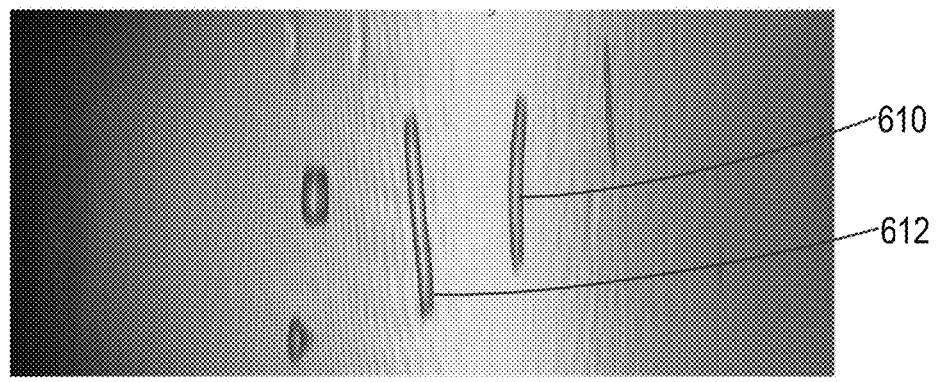
FIG. 6A illustrates an example of tubing containing contrast medium or contrast fluid as captured using MRI (magnetic resonance imaging).
Figure 6B:
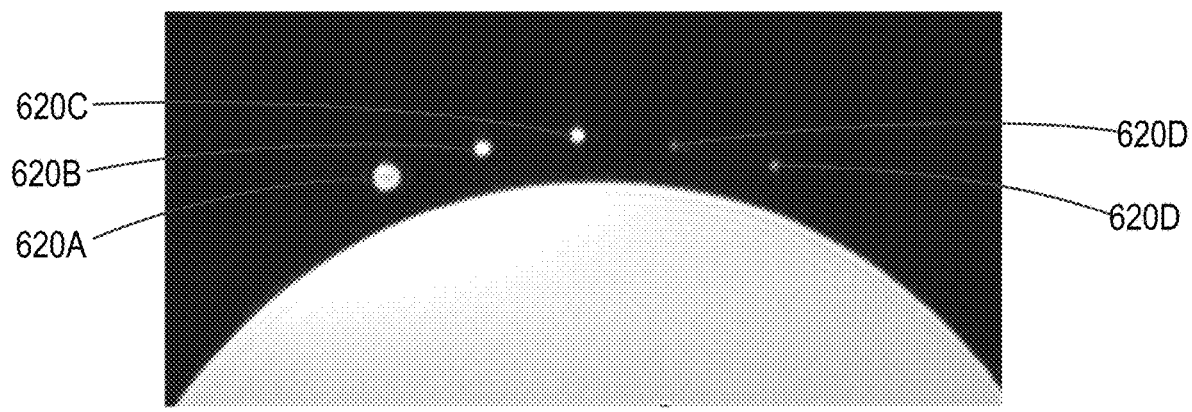
FIG. 6B illustrates an example of various diameters of tubing containing a contrast medium as captured using MRI (magnetic resonance imaging).

FIG. 6A illustrates tubing 610, 612 containing parametric fluid as captured by an MRI imaging device. The tubing in FIG. 6a has been captured over a container of contrast medium or parametric fluid. FIG. 6B illustrates multiple segments of tubing 620A-C captured in an MRI image data set. The multiple segments of tubing are being viewed from one end of the tubing. A reference container containing parametric fluid is below the segments of tubing in FIG. 6B for reference.

As discussed earlier, the ability to align the image data set with anatomical structures in a body of a patient is valuable when lining up medical instruments and performing other actions in a medical procedure. If the image data set does not line up closely to the anatomical structure or actual human tissue that was previously imaged, then the image data set is less useful in a medical procedure situation. For example, if the image data set that represents human tissue (e.g., an imaged hole in a skull) does not line up with the actual human tissue (e.g., a real hole in the skull) then the image data set is much less useful in a medical procedure. In some cases, a coarsely aligned image set may be useful for simulation or practice purposes but not for a surgical procedure. In contrast, the present technology enables alignment of an image data set for an MRI image with a degree of resolution that can allow medical personnel to use the image data set in a high precision medical procedure.

In medical image acquisition using non-optical imaging modalities, the numbers of voxels in an image may be for example, 512×512 voxels. Each voxel in the image may represent a defined number of millimeters or a sampling frequency at which the image data set is captured from the patient's body. For example, the sampling frequency may be expected to be 1.2 millimeters per voxel (Note: This is an arbitrary measurement example and actual sampling frequencies may vary). However, if a medical image scanner is slightly mis-calibrated and the sampling of voxels in image data set actually occurs at 1.15 millimeters per voxel, then the real size of the human anatomy or real human tissues being imaged is different than what the image data set or image scanner may capture (e.g., the image data set may be too small). Such a mis-calibration may result in the virtual human tissue being a little bigger or little smaller than the actual human tissue which is a result of inaccurate sampling.

As a result, the present technology can use an image visible marker to scale the image data set(s) being displayed to a user of the AR headset. More accurate scaling can help reduce image distortion and correct other errors. The image visible marker can be identified in the image data set which includes the captured version or electronic version of the image visible marker. The actual size of the image visible marker may have been measured prior to the medical procedure or the actual size of the image visible marker may be known in advance at manufacturing time. Alternatively, the size of the image visible marker may be measured from a visible light image (i.e., photos or video) captured by a camera of the AR headset. For example, the size of the image visible marker may be measured in the images captured by the camera using reference object (e.g., an optical code or medical instrument) or other means.

A comparison can be made between the known size of the image visible marker in the real world and the measured size of the image visible marker data captured in the image data set. The comparison can determine if there is an error or difference in size between the electronic representation of image visible marker in the image data set and the known size of the image visible marker. If a difference is identified, then the image data set can be scaled to correct for that difference or error. Correcting for a scaling issue in the image data set results in the image data set being able to be better used in a medical procedure. This technology can correct any incorrect image scaling by increasing or decreasing the scaling of the images. For example, if the image data set size is off by 5% and a medical surgery is being performed where a needle penetrates and travels through human tissue for 20 cm, then the tip of the needle might be 1 cm off at the destination location in the human tissue in the surgery. Missing a desired location by 1 cm in a surgery is a significant amount in the human body and may have serious consequences for the individual patient. When the image data is scaled correctly and aligned accurately, then such problems in medical procedures may be reduced.

Figure 7:
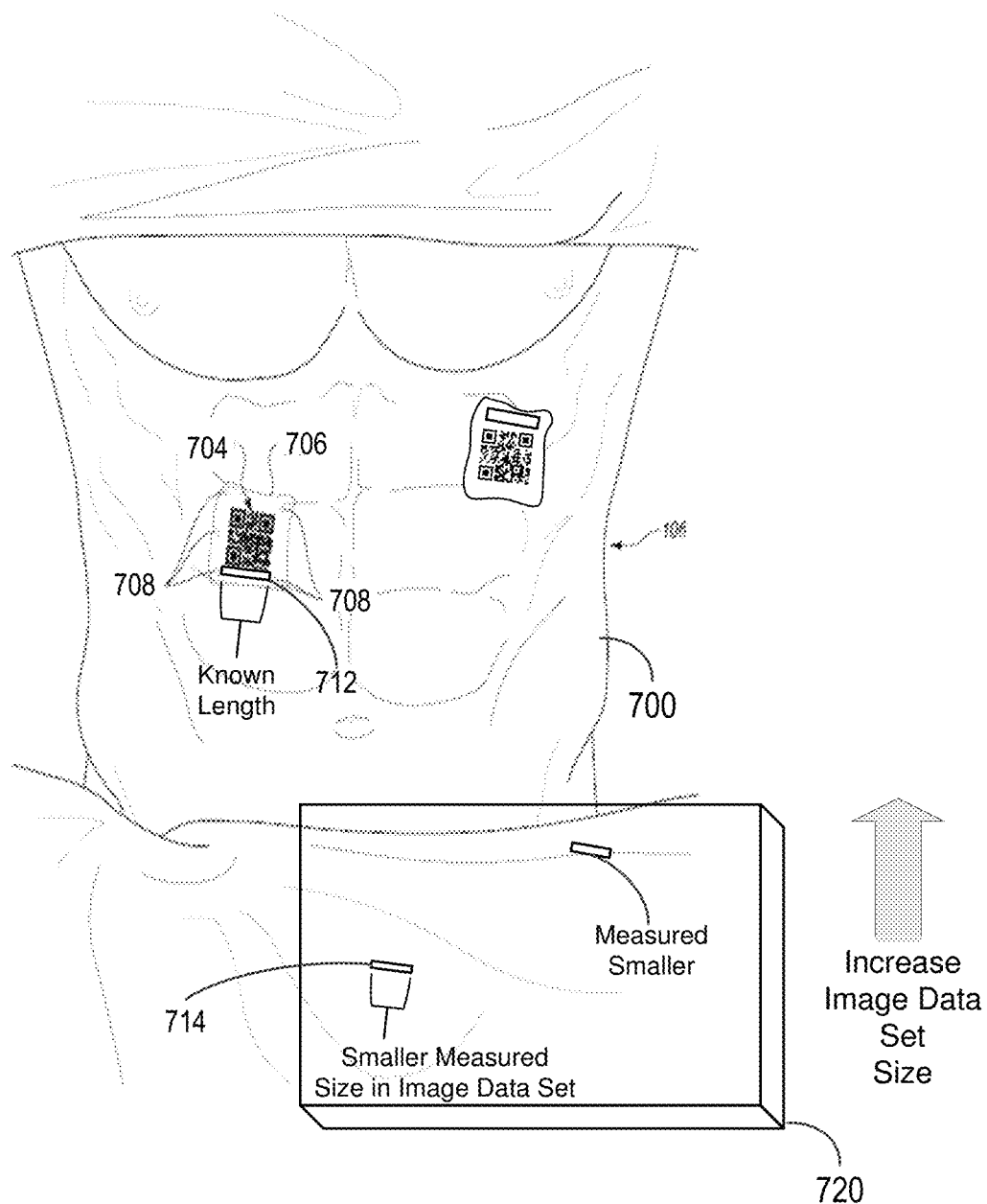
FIG. 7 illustrates the scaling of an image data set by comparing a measured size of the image visible marker (e.g., gadolinium fluid in tubing) in a captured image data set to a known or measured size of the image visible marker.

FIG. 7 illustrates this scaling of an image data set 720 by comparing a measured size of the image visible marker 714 (e.g., gadolinium tubing) in the captured image data set 720 to the known size of the image visible marker 712 or the measured size of the image visible marker.

A known size of a geometric attribute of the image visible marker may be identified. The geometric attribute of the optical code can be: a length of a tubing containing a parametric fluid, a distance between two metallic markers 708 attached to the optical code 704, a radius of a circle encompassing multiple metallic markers of the optical code, a diameter of the image visible marker, or another geometric measurement of the image visible marker. The known size of the geometric attribute may be obtained from a data store that stores a known size of the geometric attribute that was previously measured using a physical measuring device by a medical technician or the known size was set a manufacturing time. For example, the size of the geometric attribute of the optical code can be a pre-measured value stored in a data store accessible to the AR headset. As discussed earlier, the known size of the geometric attribute of the image visible marker may be measured using a visual image or photo captured of the optical code and image visible marker using a visible light camera of the AR headset. This assumes the image visible mark is viewable using the AR headset camera which is not always true.

A measured size of the geometric attribute of the image visible marker in the image data set can be compared to the known size of a geometric attribute of an image visible marker to determine a computed difference in size between a measured size of the geometric attribute of the image visible marker in the image data set and the known size of the geometric attribute of the image visible marker.

The scaling of the image data set can be modified based in part on the computed difference in size between the known size and measured size of the geometric attribute of the image visible marker. The scaling can allow the image data set to be more accurately aligned with the body of the person using one or more optical codes on the body of the person as viewed through the AR headset and the image visible marker. The modification of the scaling can be either increasing or decreasing the scaling of the image data set to match the measured size of the geometric attribute of the image visible marker in the image data set to the known size of the geometric attribute of the image visible marker.

More specifically, the scaling of the image data set as viewed through the AR headset may be increased where the known size of a geometric attribute of the optical code is greater than the measured size of the image visible marker in the image data set. Conversely, the scaling of the image data set can be decreased as viewed through the AR headset, where the known size of the geometric attribute of the optical code is smaller than the measured size of the image visible marker in the image data set.

This technology enables a computed calibration or a calibration between the known size of an object and a measured size of an object in an image data set without necessarily needing intervention from medical personnel during a medical procedure. For example, the known length of an image visible marker may be 10 millimeters. The image visible marker may be found in the MR image and a measure of the image visible marker may be made using electronic tools in imaging software. The system can then compare the size of the image visible marker to the known size of the object in the image data set. If the image visible marker is too small or too large in the image data set, then we can determine the image is too zoomed-in or too zoomed-out, and as a result the image data set can then be automatically scaled to match the actual size of the image visible marker or optical code. This scaling will in turn match the image data set to the correct real world size of the body of the patient or real human tissue.

In another configuration of the technology, the measurement of multiple image visible markers that have been manufactured to be the same size may be taken from an image data set. If there are expected minor errors or discrepancies in the size or length of the image visible markers as often occurs in the real world (e.g., for 5 markers that are each expected to be 10 mm long tubing), then an average of multiple image visible markers may be averaged together to find the average size of the markers. As a result, a calculation may be made to determine that the image data set is too big or too small on average (e.g., 0.5 mm, 1 mm, or 3 mm off in scaling based on the average of 5 markers) and the image data set does not fit the measured values that are either known in advance or are measured from an image captured by a camera. Thus, the scaling and the comparison discussed above can occur based on the average size of the image visible makers.

This scaling aspect of the technology can also apply to the use of image visible radiopaque materials that are for use with other imaging modalities besides MRI. For example, radiopaque material can be printed on an optical code. Examples of radiopaque material may include, but are not limited to: metal spheres, liquid spheres, radiopaque plastic, metal impregnated rubber, metal strips, paramagnetic material, and sections of metallic ink. The radiopaque material may be printed to a resolution of less than a one tenth of a millimeter (0.1 mm). The techniques described above for scaling can be used with radiopaque markers for many types of imaging modalities such as X-ray, CT scans, or other imaging modalities that can acquire image data sets containing image visible markers. A more detailed list of examples of non-optical imaging modality to which scaling and image visible markers may be applied may be a Computerized Tomography (CT) scan modality, an X-ray modality, a Positron Emission Tomography (PET) modality, an ultrasound modality, a fluorescence modality, an Infrared Thermography (IRT) modality, 3D Mammography, or a Single-Photon Emission Computed Tomography (SPECT) scan modality. For example, the image visible marker used in other modalities may be a radiopaque marker, an echogenic structure for ultrasound, a contrast medium or a contrast agent in tubing, etc.

In one configuration of the technology, when a patient's body is being viewed through the AR headset, the system can identify optical codes (e.g., AprilTags) on the patient's body as one or more points in space, and it is desirable to know the points of the optical code (e.g., AprilTag) down to sub-millimeter accuracy. However, an optical code is not a single point in space because the optical code covers many points in space. As a result, when the optical code is viewed through AR headset there may be perspective problems, optics imperfections, parallax problems and foreshortening which occur when viewing and identifying the location of the optical code and the related 3D points. As a more specific example, the distance from the optical sensor or camera on the AR headset from a first point on the optical code may be farther than a second point on the optical code and this may shift the localization of an image data set with respect to a body of a patient slightly. In order to get improved millimeter and sub-millimeter accuracy in alignment, the optical codes can be treated as a single point in space rather than a group of points subject to visual distortion.

Aligning the image data set may be performed by reducing a visible optical code to a single point in space and aligning the single point with an image visible marker that has also been reduced to a second single point in the 3D space being viewed by the AR headset. Instead of using many points for the entire optical code for alignment purposes, the optical code can be identified as one point in 3D space. The coordinates of the edges (e.g., the corners or other optical code features) can be identified and mathematical lines (e.g., diagonals of a square or rectangle, bisecting lines, etc.) can be drawn between the edges of the optical code, and then optical code can be reduced to a single point in space at a point where the lines intersect.

Reducing the optical code to a single point in space can help correct the error created by parallax and geometrical distortion. The use of multiple points of an optical code for alignment may also be less accurate than using a single point. In some situations, the measurement of one or more points of the optical code, such as the corners, can vary by a couple of millimeters depending at what level the edge detection threshold is set in the AR headset or the optical distortion existing at various points in the visible image. The present technology improves alignment and can help correct the potential issues discussed earlier.

Figure 8:
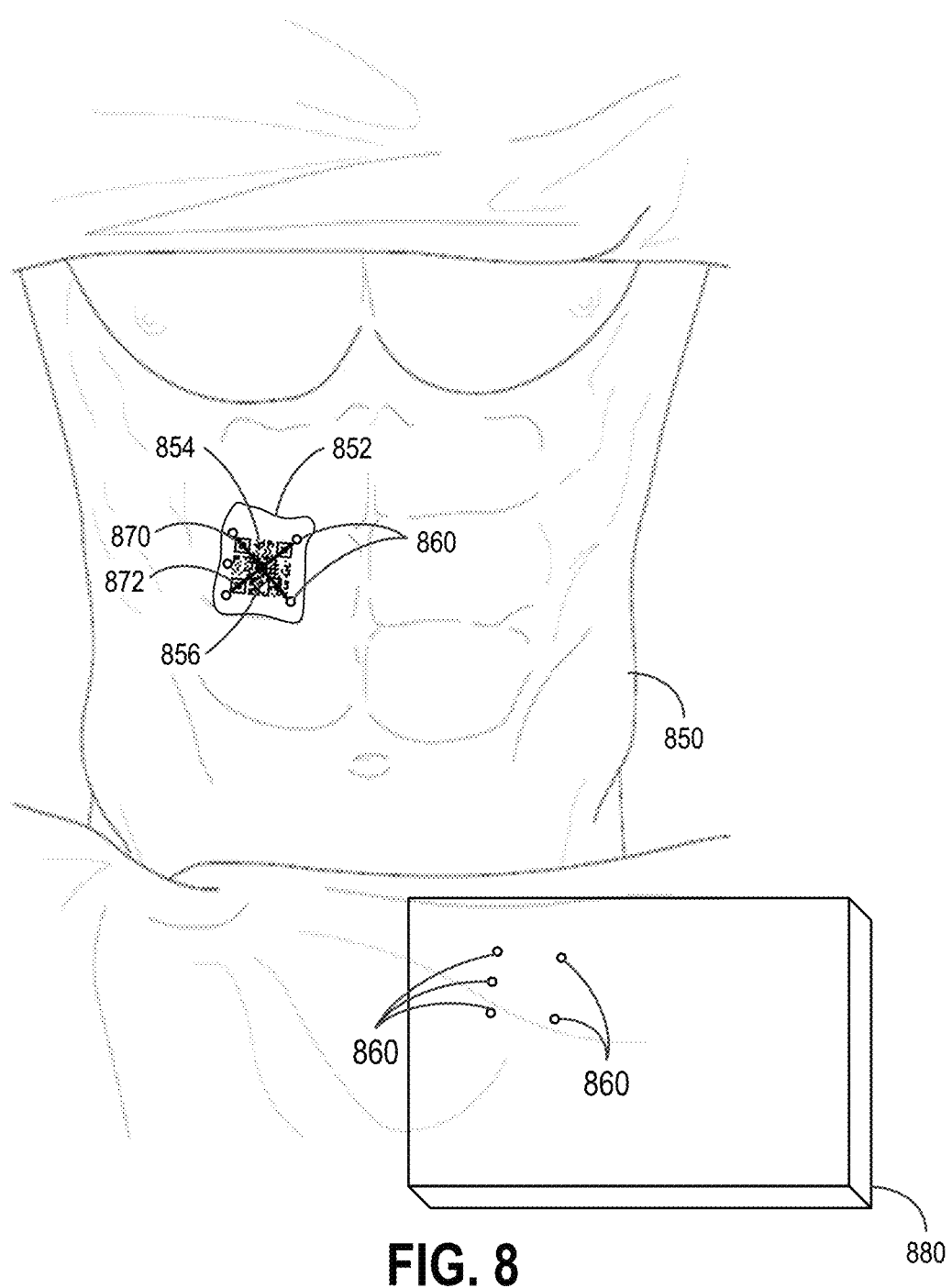
FIG. 8 illustrates finding and using the center of an optical code for alignment or co-localization of an image data set with a body of a person using an augmented reality (AR) headset.

FIG. 8 illustrates finding and using the center of an optical code 854 for alignment or co-localization of an image data set 880 with a body 850 of a person using an augmented reality (AR) headset. One or more optical codes 854 which are printed on material 852 and are associated with the body of the person may be identified in a camera image captured by a visible light camera of an AR headset. The optical code on a body of the person 850 may located in a fixed position relative to an image visible marker 860 (e.g., tubing or a radiopaque material).

One or more edges of an optical code 854 associated with the body of the person 850 in the visual image data may also be identified. A center point 856 of the optical code may be identified using the one or more edges of the optical code 854.

One method for computing the center, geometric center or centroid of the optical code 854 may be calculating a first line between a first point on the edge of the optical code and a second point on edge of the optical code 854 to form a first diagonal 870 of the optical code. The first and second points may be the corners of the optical code. A second 872 line may also be computed between a third point on the edge and a fourth point on the edge (e.g., corners) of the optical code to form a second diagonal of the optical code which intersects the first line. A center point 856 of the optical code where the first line and second line intersect can then be determined. The image data set can be aligned with the body of the person using the center point of the optical code and the image visible code, since the distance between the image visible code and the center of the optical code is fixed and known.

In one example, AprilTags may have a radiopaque ink printed on the back of the AprilTag that forms the image visible marker 860 and the radiopaque marker may be visible in CT scans, X-Rays or an imaging modality that can detect radiopaque markers. The AprilTags can be found automatically and uniquely identified because each AprilTag has a different pattern and the optical code has the image visible marker(s) 860, printed on the back of the optical code material or backing, which may be visible in the CT scan. In one example, the radiopaque material may be barium or bismuth. In addition, tubing containing paramagnetic material may also be used as an image visible marker for MR images.

Finding the center or centroid of an optical code may be computed for an optical code which is square or rectangular, as illustrated. However, the center or centroid of an optical code in any shape, such as a circle, triangle, star, hexagon, polygon, an irregular shape, or any other shape, may be computed.

Finding the centroid 866 of the optical code can correct for errors created by surface curvature on the surface of the human patient. Putting an X through a visible optical code helps to better identify a single location for the optical code to use in the alignment process despite any surface curvature in the optical code due to the optical code being attached to the surface of the patient's body. Finding the centroid using any known method can also assist with correcting for any curvature or other distortions of the optical code attached to the patient. For example, finding a centroid or other clearly defined single point of the optical code can assist with correcting alignment issues, identifying the optical code and improve precise tracking for the optical codes.

Multiple center points can also be used for alignment. In this case, the center points of a plurality of optical codes in the visual image data may be found. An average center point for the center points of the plurality of optical codes may be calculated. The image data set can be aligned with a body of a person or patient using the average center point of the plurality of optical codes.

Finding the corners of a box or rectangle containing the optical code can also be made more accurate by using QR codes, 2D bar codes, or April tags that use dark or black boxes on the corners of the optical code (as illustrated in FIG. 2). The boxes enable the corner of the optical code to be clearly identified using edge detection and this corner identification can result in determining the center coordinate of the optical code more accurately. Using the boxes or dark visual accenting at the edges of the visual codes makes identifying the corners of the visual code more invariant to a visual threshold used for finding the edge (e.g., edge detection) or changing lighting conditions.

Finding the centers of optical codes can also assist in correcting errors that might be created by contrast resolution issues and threshold detection issues. The optical codes or visual tag may be precise in printed form but once the optical code is imaged, there may be blurring or a lack of contrast. By using diagonals or bisecting lines with a square or rectangle or finding a center of a circle then the position of the optical code may be more easily determined or encoded. If the optical code were circular, then the center of circle can be found and a single point can be used for alignment, as discussed.

Finding the center point of the optical codes can also assist with more accurately capturing optical codes that are not relatively large compared to the image data set. If MR imaging is being captured in a 256×192 matrix (lower resolution as compared to CT) the optical codes are preferably not overly large compared to the size of the person because larger optical codes can have more geometrical distortion on the body of the patient. Thus, a more accurate center point can be found for a small optical code.

Figure 9A:
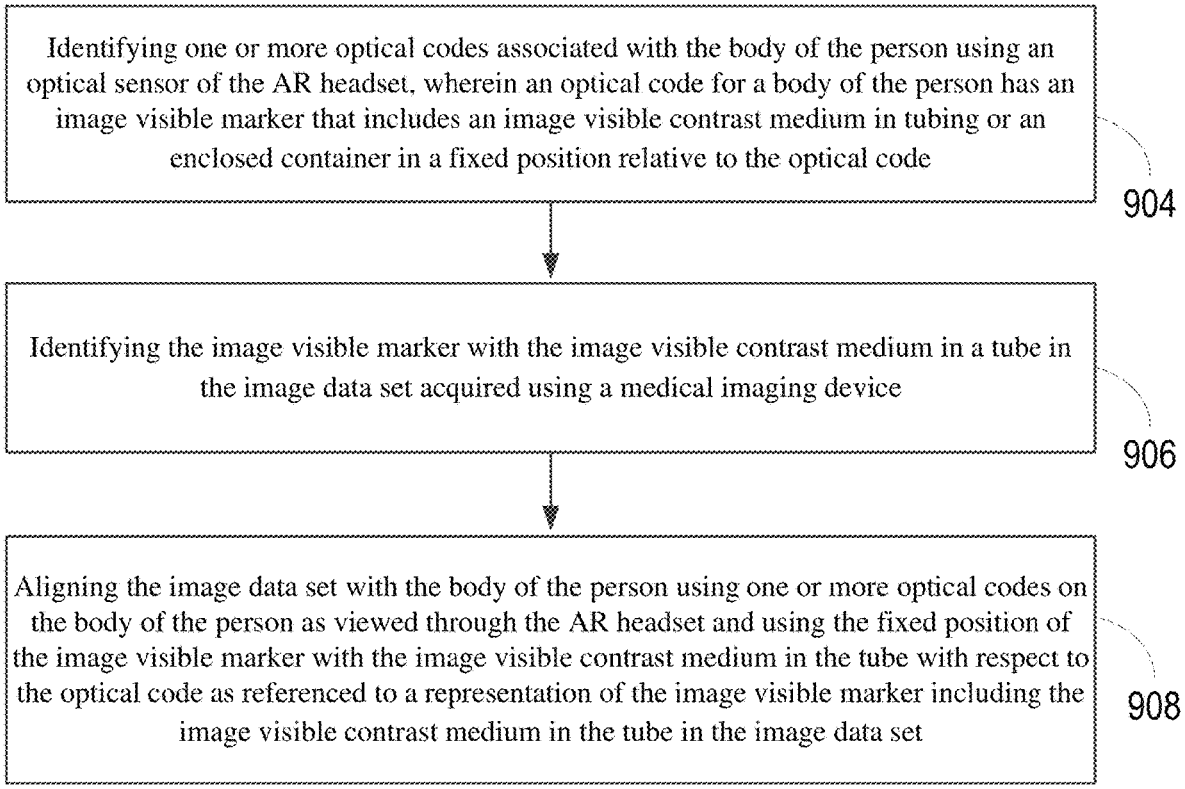
FIG. 9a is a flowchart of an example method of using an augmented reality (AR) headset to co-localize an image data set with a body of a person using an image visible marker which is tubing containing a contrast medium or marking agent.

FIG. 9a is a flowchart of an example method of using an augmented reality headset to co-localize an image data set and a body of a patient using tubing containing an image visible marking fluid. In these and other embodiments, the method may be performed by one or more processors based on one or more computer-readable instructions stored on one or more non-transitory computer-readable media.

FIG. 9a illustrates a method for using an augmented reality (AR) headset to co-localize an image data set with a body of a person. The method can include the operation of identifying one or more optical codes associated with the body of the person using an optical sensor of the AR headset, as in block 904. The optical code for a body of the person can have an image visible marker that includes an image visible contrast medium (i.e., paramagnetic fluid) in tubing or in an enclosed container in a fixed position relative to the optical code.

The image visible marker with the image visible contrast medium in the tubing can be identified in the image data set acquired using a medical imaging device (e.g., an MRI scanner), as in block 906. The image data set can be aligned with the body of the person using one or more optical codes on the body of the person as viewed through the AR headset, as in block 908. In addition, the image data set can be aligned using the fixed position of the image visible marker with the image visible contrast medium in the tubing with respect to the optical code as referenced to a representation of the image visible marker with the image visible contrast medium in the tubing in the image data set.

Figure 9B:
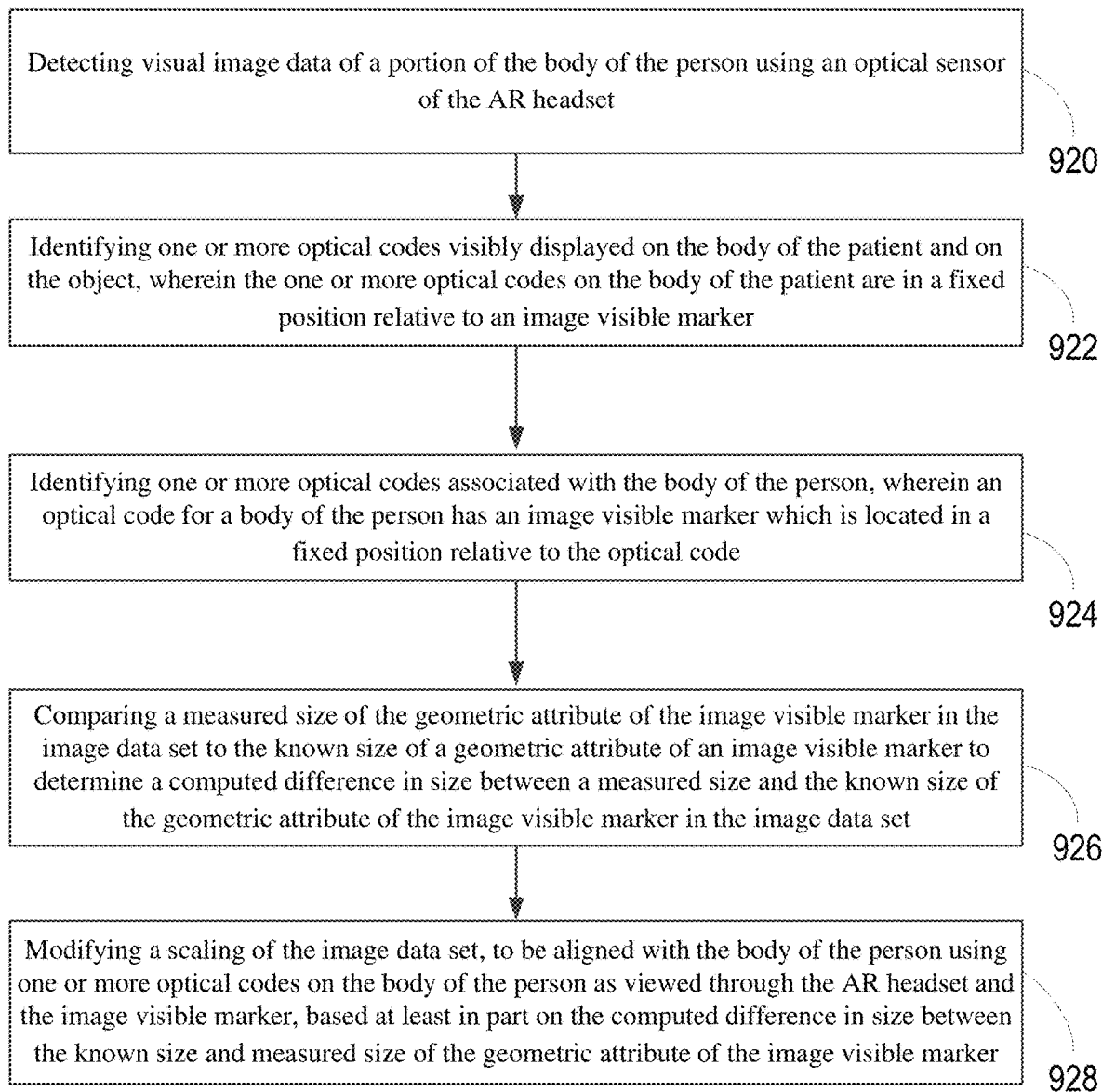
FIG. 9b illustrates a method for comparing a measured size of a geometric attribute of the image visible marker in the image data set to the known size of the geometric attribute of an image visible marker to scale an image data set aligned to a body of a person.

FIG. 9b illustrates a method for using an augmented reality (AR) headset to co-localize an image data set with a body of a person. Visual image data of a portion of the body of the person can be acquired using an optical sensor or camera of the AR headset, as in block 920. One or more optical codes associated with the body of the person can be identified in the visual image data, as in block 922. An optical code for a body of the person may have an image visible marker which is located in a fixed position relative to the optical code.

A known size of a geometric attribute of the image visible marker associated with the body of the person can be identified, as in block 920. The image visible marker may appear in the image data set, as captured using a medical imaging device.

A measured size of the geometric attribute of the image visible marker in the image data set can be compared to the known size of a geometric attribute of an image visible marker to determine a computed difference in size between a measured size and the known size of the geometric attribute of the image visible marker in the image data set, as in block 926. The scaling of the image data set may be modified, as in block 928. The image data set may be aligned with the body of the person using one or more optical codes on the body of the person as viewed through the AR headset and the image visible marker. The alignment may occur based in part on the computed difference in size between the known size and measured size of the geometric attribute of the image visible marker in the image data set.

Figure 9C:
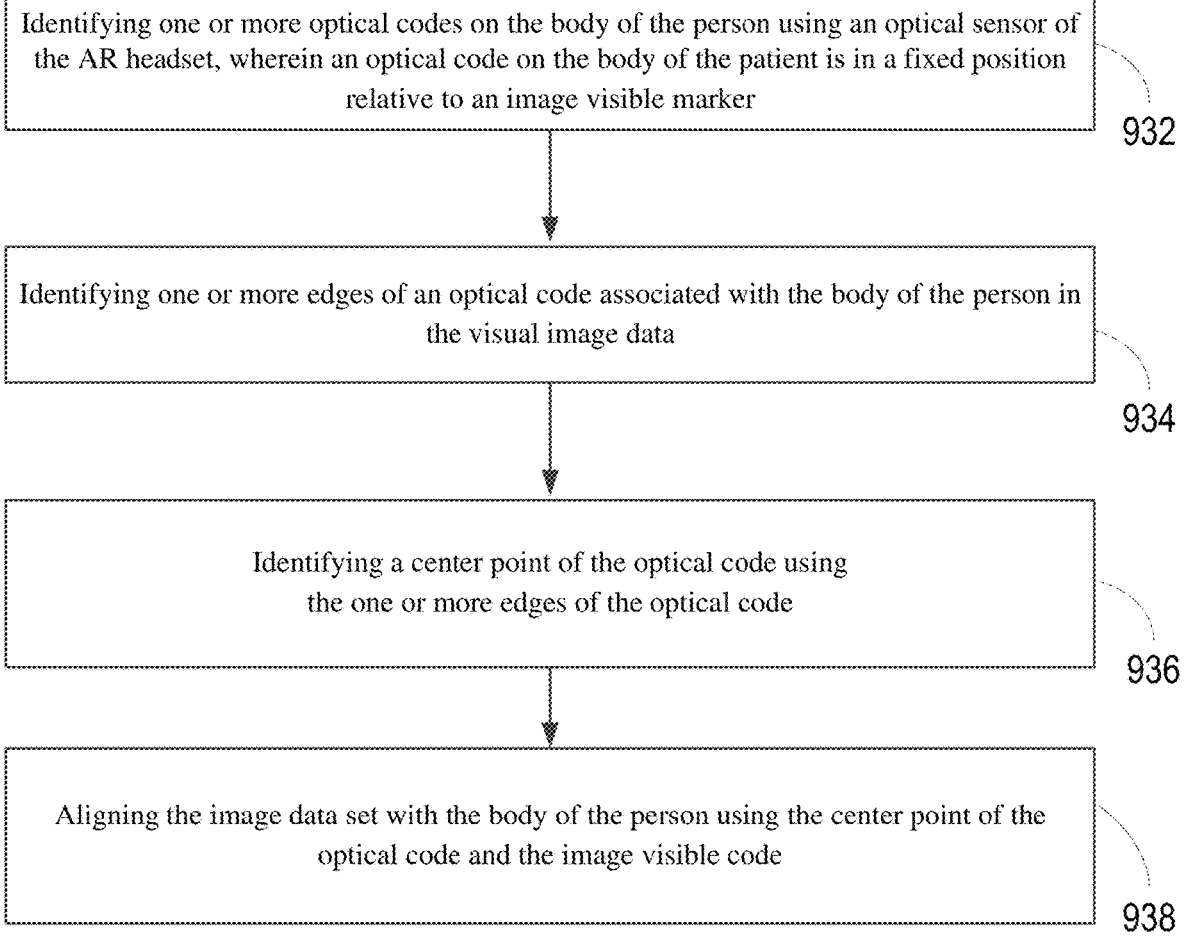
FIG. 9c illustrates a method for aligning an image data set to a body of a person by finding a center of an optical code.

FIG. 9c illustrates a method for using an augmented reality (AR) headset to co-localize an image data set with a body of a person. The method can include identifying one or more optical codes associated with the body of the person using an optical sensor of an AR headset, as in block 932. An optical code for a body of the person can be located in a fixed position relative to an image visible marker.

Edges of an optical code associated with the body of the person in the visual image data can be identified or detected, as in block 934. Points on the edges may then be selected. A center point of the optical code can be identified using the points on the one or more edges of the optical code, as in block 936. The image data set can be aligned with the body of the person using the first center point of the optical code and the second center point of the image visible code, as in block 940.

Figure 10:
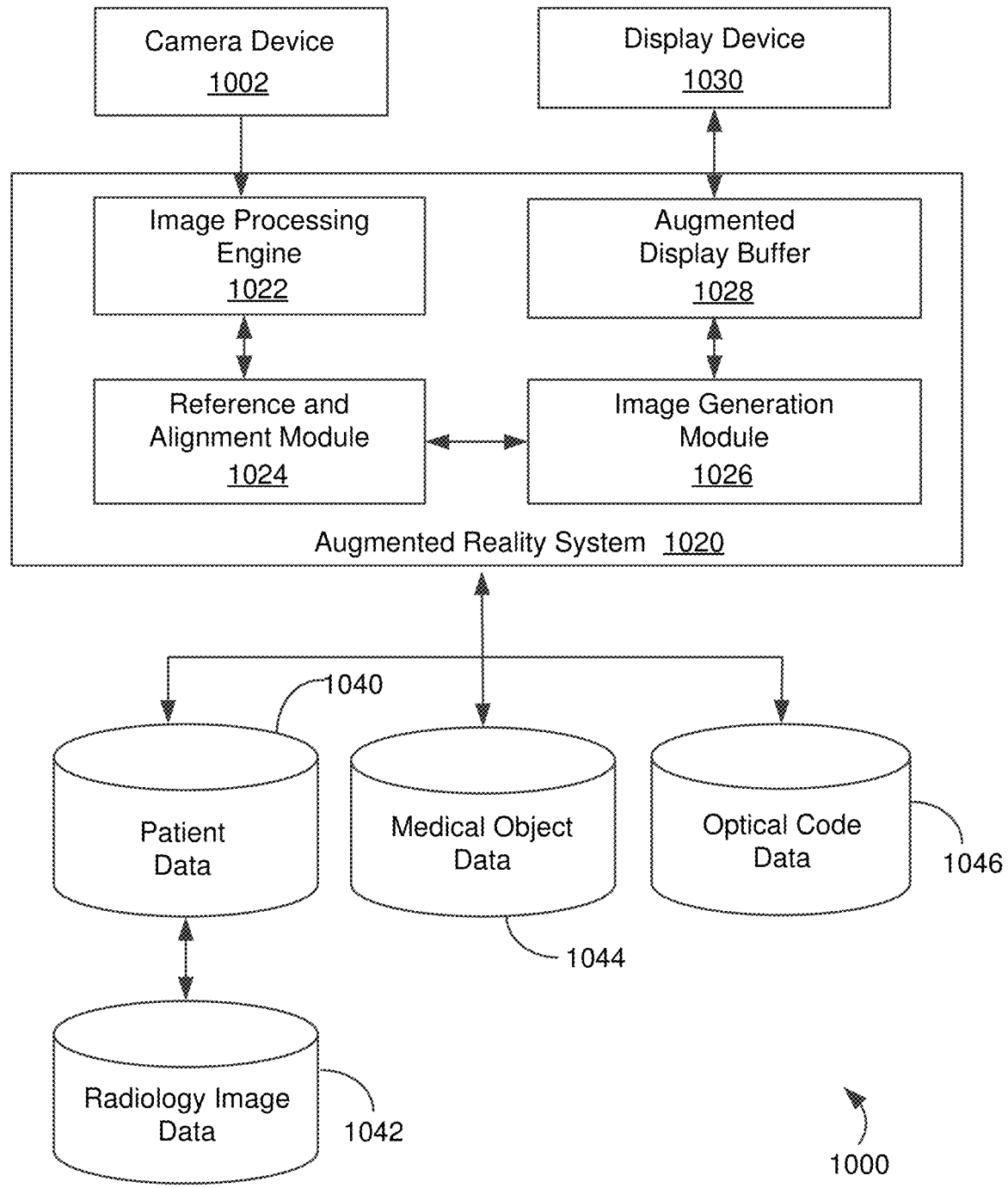
FIG. 10 illustrates an example system that may be employed for aligning an image data set to a body of a person.

FIG. 10 illustrates an example system that may be employed for using an augmented reality (AR) headset to co-localize an image data set with a body of a person which is viewed through the AR headset. The system 1000 may include a camera device 1002, an augmented reality system 1020, a display device 1030, and a plurality of databases or data stores. The system 1000 may also include one or more processors, a memory, a file system, a communication unit, an operating system, and a user interface, which may be communicatively coupled together. In some embodiments, the system 1000 may be, for example, a desktop computer, a server computer, a laptop computer, a smartphone, a tablet computer, an embedded computer, an AR headset, a VR headset, etc.

The camera device 1002 can be configured to capture visible data. In one example, the camera device 1002 may be used to capture visible data during a medical procedure or medical examination. The visible data captured by the camera device 1002 may include images of a body of a person (or a portion of a body), optical codes, image visible markers, medical implements (e.g., medical instruments, implants, and so on). The camera device 1002 may transmit the captured optical data to the augmented reality system 1020. The system also may include surface sensors, optical sensors, infrared sensors, Lidar sensors or other sensors to detect and assist with mapping a real view or actual view detected by the AR system. Any object or surface may be detected for an operating theater, a patient, a room, physical geometry, medical implements, or any other physical surroundings or objects.

The augmented reality system 1020 may include an image processing engine 1022, a reference and alignment module 1024, an image generation module 1026, and an augmented display buffer 1028. For example, the image processing engine 1022 receives the captured visible image data from the camera device 1002 and analyzes the visible image data to identify one or more optical codes, objects or people in the visible image data. A plurality of different techniques may be used to identify object or people within the visible image data including but not limited to feature extraction, segmentation, and/or object detection.

The image processing engine 1022 also identifies optical codes that may be affixed to both bodies of patients within the image. Once the image processing engine 1022 identifies an optical code (e.g., an AprilTag, a 2D bar code, a QR code, and so on) the image processing unit 1022 accesses the optical code database 1046 to retrieve information associated with the optical code. In some examples, the optical code is associated with an image visible marker of a measured size, such as a tube containing paramagnetic fluid of a measured length. In addition, the optical code may be associated with a particular patient, a particular procedure, or a particular object.

In some embodiments, the reference and alignment module 1024 engages with the image processing engine 1022 to reference a body of a person and an image data set with respect to each other, as described earlier. In addition, the reference and alignment module 1024 can use optical code information in the medical object database 1044 to properly identify the size and shape and identity of optical codes. Once the position and orientation of the body of the patient is determined, the reference and alignment controller 1026 can align any associated radiology images in the radiology image data 1042 with the body of the patient. In some examples, the radiology images are received from a radiology image database 1042 based on patient records in a patient record database 1040.

The image generation module 1026 can generate graphical data, virtual tools, a 3D surgical path, 3D colorization or shading of a mass or organ, or highlighting of a mass, organ or target to display in a display device 1030, as layered on top of the body of the patient. In some examples, this information can be loaded into an augmented display buffer 1028. This information can then be transmitted to a display device 1030 for display to a user.

In one example, the patient database 1040 includes a plurality of patient records. Each patient record can include one or more medical procedures to be performed on a patient. The patient records may also include notes, instructions or plans for a medical procedure. A patient record can also be associated with one or more radiology images in the radiology image database 1042. In some examples, the radiological images include a representation of the image visible marker that allows the reference and alignment module 1026 to properly align the image data set with the body of a patient using the fixed position of an optical code with respect to the image visible marker. In one example, the medical object data 1044 includes information describing the medical implements, including medical instruments, implants, and other objects.

In some embodiments, the augmented reality system may be located on a server and may be any computer system capable of functioning in connection with an AR headset or display device 1030. In such embodiments, the server may be configured to communicate via a computer network with the AR headset in order to convey image data to, or receive data from, the AR headset.

Figure 11:
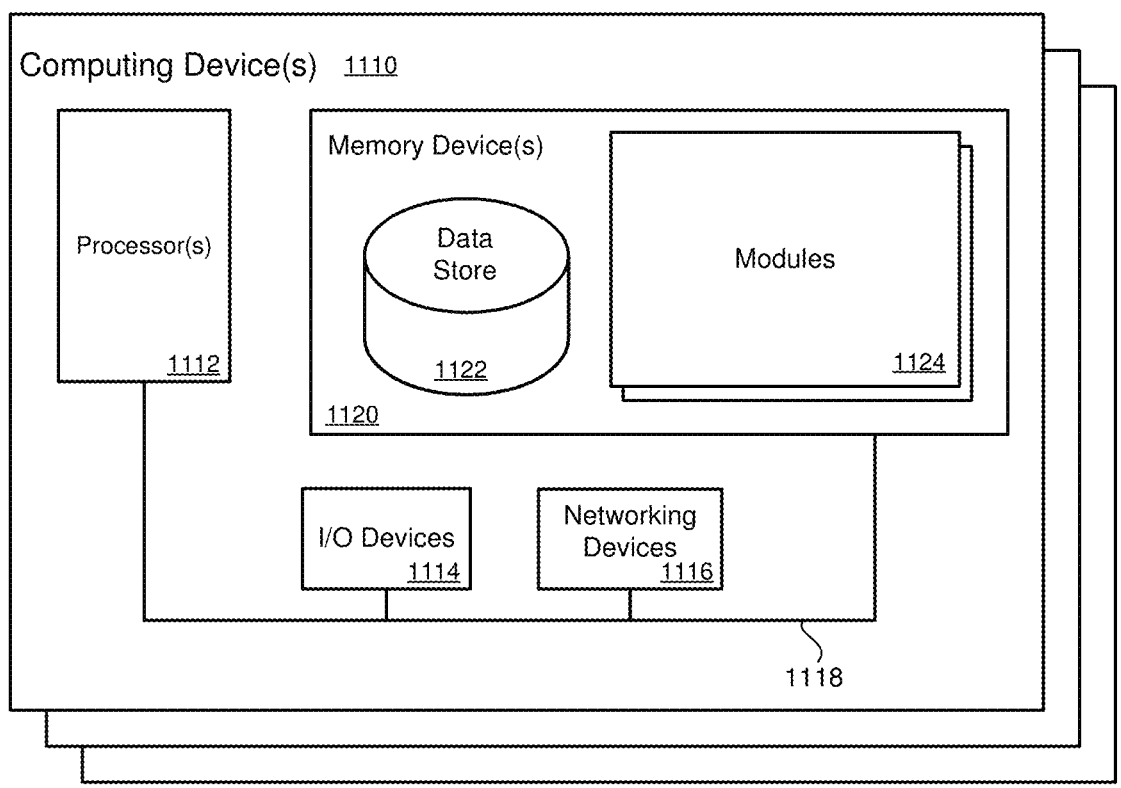
FIG. 11 is a block diagram illustrating an example of a computing system to process the present technology.

FIG. 11 illustrates a computing device 1110 on which modules of this technology may execute. A computing device 1110 is illustrated on which a high level example of the technology may be executed. The computing device 1110 may include one or more processors 1112 that are in communication with memory devices 1112. The computing device may include a local communication interface 1118 for the components in the computing device. For example, the local communication interface may be a local data bus and/or any related address or control busses as may be desired.

The memory device 1112 may contain modules 1124 that are executable by the processor(s) 1112 and data for the modules 1124. The modules 1124 may execute the functions described earlier. A data store 1122 may also be located in the memory device 1112 for storing data related to the modules 1124 and other applications along with an operating system that is executable by the processor(s) 1112.

Other applications may also be stored in the memory device 1112 and may be executable by the processor(s) 1112. Components or modules discussed in this description that may be implemented in the form of software using high programming level languages that are compiled, interpreted or executed using a hybrid of the methods.

The computing device may also have access to I/O (input/output) devices 1114 that are usable by the computing devices. An example of an I/O device is a display screen that is available to display output from the computing devices. Other known I/O device may be used with the computing device as desired. Networking devices 1116 and similar communication devices may be included in the computing device. The networking devices 1116 may be wired or wireless networking devices that connect to the internet, a LAN, WAN, or other computing network.

The components or modules that are shown as being stored in the memory device 1112 may be executed by the processor 1112. The term "executable" may mean a program file that is in a form that may be executed by a processor 1112. For example, a program in a higher level language may be compiled into machine code in a format that may be loaded into a random access portion of the memory device 1112 and executed by the processor 1112, or source code may be loaded by another executable program and interpreted to generate instructions in a random access portion of the memory to be executed by a processor. The executable program may be stored in any portion or component of the memory device 1112. For example, the memory device 1112 may be random access memory (RAM), read only memory (ROM), flash memory, a solid state drive, memory card, a hard drive, optical disk, floppy disk, magnetic tape, or any other memory components.

The processor 1112 may represent multiple processors and the memory 1112 may represent multiple memory units that operate in parallel to the processing circuits. This may provide parallel processing channels for the processes and data in the system. The local interface 1118 may be used as a network to facilitate communication between any of the multiple processors and multiple memories. The local interface 1118 may use additional systems designed for coordinating communication such as load balancing, bulk data transfer, and similar systems.

Some of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, comprise one or more blocks of computer instructions, which may be organized as an object, procedure, or function. Nevertheless, the executables of an identified module need not be physically located together, but may comprise disparate instructions stored in different locations which comprise the module and achieve the stated purpose for the module when joined logically together.

Indeed, a module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices. The modules may be passive or active, including agents operable to perform desired functions.

The technology described here can also be stored on a computer readable storage medium that includes volatile and non-volatile, removable and non-removable media implemented with any technology for the storage of information such as computer readable instructions, data structures, program modules, or other data. Computer readable storage media include, but is not limited to, RAM, ROM, EEPROM, flash memory or other memory technology, CD-ROM, digital versatile disks (DVD) or other optical storage, magnetic cassettes, magnetic tapes, magnetic disk storage or other magnetic storage devices, or any other computer storage medium which can be used to store the desired information and described technology.

The devices described herein may also contain communication connections or networking apparatus and networking connections that allow the devices to communicate with other devices. Communication connections are an example of communication media. Communication media typically embodies computer readable instructions, data structures, program modules and other data in a modulated data signal such as a carrier wave or other transport mechanism and includes any information delivery media. A "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency, infrared, and other wireless media. The term computer readable media as used herein includes communication media.

Reference was made to the examples illustrated in the drawings, and specific language was used herein to describe the same. It will nevertheless be understood that no limitation of the scope of the technology is thereby intended. Alterations and further modifications of the features illustrated herein, and additional applications of the examples as illustrated herein, which would occur to one skilled in the relevant art and having possession of this disclosure, are to be considered within the scope of the description.

Furthermore, the described features, structures, or characteristics may be combined in any suitable manner in one or more examples. In the preceding description, numerous specific details were provided, such as examples of various configurations to provide a thorough understanding of examples of the described technology. One skilled in the relevant art will recognize, however, that the technology can be practiced without one or more of the specific details, or with other methods, components, devices, etc. In other instances, well-known structures or operations are not shown or described in detail to avoid obscuring aspects of the technology.

Although the subject matter has been described in language specific to structural features and/or operations, it is to be understood that the subject matter defined in the appended claims is not necessarily limited to the specific features and operations described above. Rather, the specific features and acts described above are disclosed as example forms of implementing the claims. Numerous modifications and alternative arrangements can be devised without departing from the spirit and scope of the described technology.

What is claimed is:

1. A method, comprising:
   identifying one or more optical codes associated with a body of a person using a sensor of an AR (augmented reality) headset, wherein an optical code for the body of the person has an image visible marker that includes an image visible contrast medium in a container in a position relative to the optical code;
   identifying the image visible marker with the image visible contrast medium in the container in an image data set acquired using a medical imaging device; and
   aligning the image data set with the body of the person using one or more optical codes as viewed through the AR headset and using the image visible marker with respect to the optical code as referenced to a representation of the image visible marker in the image data set.

2. The method of claim 1, further wherein the image visible contrast medium is an MRI (magnetic resonance imaging) visible contrast medium.

3. The method of claim 2, wherein the image visible contrast medium is a paramagnetic fluid.

4. The method of claim 2, wherein the image visible contrast medium is encapsulated in a tubing of a defined length or a tubing of variable length.

5. The method of claim 4, wherein the defined length of the tubing identifies an optical code with a defined 2D data encoding that is visible using an optical sensor of the AR headset.

6. The method of claim 5 further comprising associating the defined length of the tubing with an optical code visible using the optical sensor of the AR headset by linking the defined length of the tubing with the optical code in a data store.

7. The method as in claim 4, wherein the tubing is a shaped tubing in a shape of at least one of: a line, a cross formation, concentric circles, or a grid formation.

8. The method as in claim 4, wherein the tubing has two dimensional (2D) cross-sectional shape that is at least one of: round, triangular, square, rectangular, elliptical, hexagonal, octagonal, oval, or polygonal.

9. The method as in claim 4, wherein the tubing is a plurality of tubing segments each having a separate length.

10. The method of claim 1, wherein the image visible contrast medium is a gadolinium solution, copper sulfate, iron solution, manganese, vitamin E oil, or a paramagnetic material.

11. The method of claim 1, further comprising retrieving the image data set automatically for the body of the person using one or more optical codes on the body of the person.

12. The method of claim 4, wherein the tubing is at least one of: plastic tubing, glass, or a non-metal tubing.

13. A method, comprising:
    identifying one or more optical codes associated with a body of a person, wherein an optical code for the body of the person has an image visible marker which is located in a position relative to the optical code;

identifying a known size of a geometric attribute of the image visible marker, which appears in an image data set;

comparing a measured size of the geometric attribute of the image visible marker in the image data set to the known size of a geometric attribute of an image visible marker to determine a computed difference in size between the measured size and the known size of the geometric attribute of the image visible marker in the image data set; and modifying a scaling of the image data set as viewed through an AR (augmented reality) headset using the image visible marker, based at least in part on the computed difference in size.

14. The method as in claim 13, further comprising increasing or decreasing the scaling of the image data set to match the measured size of the geometric attribute of the image visible marker in the image data set to the known size of the geometric attribute of the image visible marker.

15. The method as in claim 13, further comprising increasing the scaling of the image data set as viewed through the AR headset where the known size of the optical code is greater than the measured size of the image visible marker in the image data set.

16. The method as in claim 13, further comprising decreasing the scaling of the image data set as viewed through the AR headset where the known size of the optical code is smaller than the measured size of the image visible marker in the image data set.

17. The method as in claim 13, wherein the size of the geometric attribute is a pre-measured value stored in a data store accessible to the AR headset.

18. The method as in claim 13, wherein the size of the geometric attribute is measured from an image visible marker that is visible on a person's body acquired by the AR headset.

19. The method as in claim 13, wherein the geometric attribute of the optical code is at least one of: a length of a tubing of a paramagnetic marker, a distance between two metallic markers with the optical code, a radius encompassing multiple metallic markers of the optical code, a diameter of the image visible marker, or a geometric measurement of the image visible marker.

20. A method, comprising:
identifying one or more optical codes associated with a body of a person using a sensor of an AR (augmented reality) headset, wherein an optical code is located in a position relative to an image visible marker;
identifying one or more edges of an optical code;
identifying a center point of the optical code using the one or more edges of the optical code; and
aligning an image data set with the body of the person based at least in part on the center point of the optical code and the position of the image visible marker relative to the optical code.

21. The method as in claim 20, wherein the center point is a computed centroid of the optical code.

22. The method as in claim 20, further comprising:
calculating a first line between a first point on an edge of the optical code and a second point on edge of the optical code to form a first diagonal of the optical code;
computing a second line between a third point on the edge and a fourth point on the edge of the optical code which forms a second diagonal of the optical code and intersects the first line; and
identifying a center point of the optical code where the first line and second line intersect.

23. A method, comprising:
identifying a plurality of optical codes associated with a body of a person using a sensor of the AR (augmented reality) headset, wherein the optical codes for the body of the person are positioned relative to an image visible marker;
identifying one or more edges of the plurality of optical codes;
finding center points of a plurality of optical codes using the one or more edges of the optical codes;
calculating an average center point of the center points of the plurality of optical codes; and
aligning an image data set with the body of the person using the AR headset, the average center point of the plurality of optical codes and image visible markers.

24. The method as in claim 23, further comprising determining a location for displaying the image data set through the AR headset by using the average center point of the plurality of optical codes as referenced to image visible markers, wherein there is a fixed distance between a center point of each optical code and each image visible marker.

* * * * *